(12) United States Patent
DaSilva

(10) Patent No.: US 11,529,162 B2
(45) Date of Patent: Dec. 20, 2022

(54) SYSTEMS, METHODS, AND DEVICES FOR ENDOSCOPIC NERVE RELEASE

(71) Applicant: Manuel F. DaSilva, East Greenwich, RI (US)

(72) Inventor: Manuel F. DaSilva, East Greenwich, RI (US)

( * ) Notice: Subject to any disclaimer, the term of this patent is extended or adjusted under 35 U.S.C. 154(b) by 193 days.

(21) Appl. No.: 16/564,304

(22) Filed: Sep. 9, 2019

(65) Prior Publication Data

US 2020/0197040 A1      Jun. 25, 2020

Related U.S. Application Data

(63) Continuation of application No. 14/938,675, filed on Nov. 11, 2015, now Pat. No. 10,448,965.

(60) Provisional application No. 62/078,739, filed on Nov. 12, 2014.

(51) Int. Cl.
| | |
|---|---|
| *A61B 17/32* | (2006.01) |
| *A61B 17/02* | (2006.01) |
| *A61B 17/00* | (2006.01) |
| *A61B 90/00* | (2016.01) |

(52) U.S. Cl.
CPC ...... *A61B 17/320036* (2013.01); *A61B 17/02* (2013.01); *A61B 17/320016* (2013.01); *A61B 90/37* (2016.02); *A61B 2017/00296* (2013.01)

(58) Field of Classification Search
CPC ............ A61B 17/320036; A61B 17/02; A61B 17/320016; A61B 17/3211; A61B 17/3201; A61B 17/3213; A61B 2018/1412; A61B 5/4893; A61B 17/0467; A61B 2017/32116
See application file for complete search history.

(56) References Cited

U.S. PATENT DOCUMENTS

| | | |
|---|---|---|
| 3,945,117 A | 3/1976 | Beaver |
| 4,026,295 A | 5/1977 | Lieberman |
| 4,173,071 A | 11/1979 | Ishida |
| 4,365,957 A | 12/1982 | Das |
| 5,306,284 A | 4/1994 | Agee et al. |
| 5,325,883 A | 7/1994 | Orr |
| 5,334,214 A | 8/1994 | Putnam |
| 5,353,812 A | 10/1994 | Chow |
| D353,002 S | 11/1994 | Tovey |

(Continued)

*Primary Examiner* — Kelly J Bekker
*Assistant Examiner* — Mikail A Mannan
(74) *Attorney, Agent, or Firm* — Knobbe, Martens, Olson & Bear, LLP

(57) ABSTRACT

A system and method for nerve decompression comprise a knife unit having a parallel upper limb and lower limb terminating proximally at the cap of the tubular sheath and a triangular shaped surgical cutting blade disposed vertically in between the upper limb and the lower limb. Upper limb and lower limb extend distally beyond the cutting blade and have open slots to facilitate proper positioning and engaging of the tissue while allowing visualization of less routing structure. The knife receives the probe head of an endoscope just behind cutting blade for proper visualization and illumination. The guiding system comprises a handle unit and a pair of parallel guides with long open slots that act as a cannula of adjustable diameter. The open slots on parallel guides facilitate 360 degree visualization of the surroundings and also prevent derailing of endoscopic knife unit while passing through it.

17 Claims, 19 Drawing Sheets

(56) References Cited

U.S. PATENT DOCUMENTS

| | | | |
|---|---|---|---|
| 5,366,465 A | 11/1994 | Mirza | |
| 5,387,222 A | 2/1995 | Strickland | |
| 5,387,223 A | 2/1995 | Agee et al. | |
| 5,413,580 A | 5/1995 | Stephenson | |
| 5,431,153 A | 7/1995 | Lee | |
| 5,458,611 A | 10/1995 | Resnick et al. | |
| 5,480,408 A | 1/1996 | Chow | |
| 5,507,800 A | 4/1996 | Strickland | |
| 5,569,283 A | 10/1996 | Green et al. | |
| 5,613,976 A | 3/1997 | Agee et al. | |
| 5,649,937 A * | 7/1997 | Bito | A61B 17/1285 606/151 |
| 5,649,946 A | 7/1997 | Bramlet | |
| D383,841 S | 9/1997 | Runciman | |
| 5,730,749 A | 3/1998 | Battenfield | |
| 5,769,865 A | 6/1998 | Kermode et al. | |
| 5,782,850 A | 7/1998 | Ro | |
| 5,827,311 A | 10/1998 | Berelsman et al. | |
| 5,893,861 A | 4/1999 | Yumoto | |
| 5,908,431 A | 6/1999 | Battenfield | |
| 5,908,433 A | 6/1999 | Eager et al. | |
| 5,957,944 A | 9/1999 | Khuri et al. | |
| 5,968,061 A | 10/1999 | Mirza | |
| 5,984,939 A * | 11/1999 | Yoon | A61B 17/12013 606/139 |
| 6,019,774 A | 2/2000 | Weiss et al. | |
| 6,179,852 B1 | 1/2001 | Strickland et al. | |
| 6,254,621 B1 | 7/2001 | Shackelford et al. | |
| 6,685,717 B1 | 2/2004 | Ilic | |
| 6,761,725 B1 | 7/2004 | Grayzel et al. | |
| 7,041,115 B2 | 5/2006 | Mirza et al. | |
| D547,451 S | 7/2007 | Asfora | |
| 7,901,404 B2 | 3/2011 | Reay-Young | |
| 9,131,951 B2 | 9/2015 | Mirza et al. | |
| 9,144,433 B2 | 9/2015 | Mirza et al. | |
| 9,179,930 B2 | 11/2015 | Mirza et al. | |
| 2004/0002629 A1 | 1/2004 | Branch et al. | |
| 2004/0054378 A1 | 3/2004 | Yang | |
| 2004/0267243 A1 | 12/2004 | Klotz et al. | |
| 2006/0190021 A1 | 8/2006 | Hausman et al. | |
| 2007/0173831 A1 | 7/2007 | Abdou | |
| 2007/0276370 A1 | 11/2007 | Altarac et al. | |
| 2007/0288043 A1 | 12/2007 | Rehnke | |
| 2009/0177205 A1 | 7/2009 | McCormack et al. | |
| 2011/0130779 A1 | 6/2011 | Mirza et al. | |
| 2013/0153628 A1 | 6/2013 | Euteneuer | |
| 2014/0066963 A1 | 3/2014 | Mirza et al. | |
| 2014/0182140 A1 * | 7/2014 | Rosenhan | A61B 17/3213 30/162 |
| 2014/0243592 A1 * | 8/2014 | Kato | A61M 25/0147 600/104 |
| 2014/0371526 A1 | 12/2014 | Mirza et al. | |
| 2015/0048142 A1 * | 2/2015 | Scheib | A61B 17/068 227/180.1 |
| 2015/0342632 A1 | 12/2015 | Mirza et al. | |
| 2017/0042566 A1 | 2/2017 | Mirza et al. | |
| 2017/0143364 A1 | 5/2017 | Mirza et al. | |

* cited by examiner

SYSTEMS, METHODS, AND DEVICES FOR ENDOSCOPIC NERVE RELEASE

CROSS-REFERENCE TO RELATED APPLICATIONS

This application is a continuation of U.S. patent application Ser. No. 14/938,675, titled SYSTEMS, METHODS, AND DEVICES FOR ENDOSCOPIC NERVE RELEASE, filed on Nov. 11, 2015, which claims the benefit of U.S. Provisional Application No. 62/078,739, titled METHOD AND SYSTEM FOR ENDOSCOPIC NERVE RELEASE, filed on Nov. 12, 2014. Each of the foregoing applications is hereby incorporated by reference herein in its entirety.

BACKGROUND

Field

The present disclosure relates generally to a surgical device for and a method of performing endoscopic surgery. More specifically, the present disclosure relates to endoscopic surgical devices and a method for use in minimally invasive surgical procedures to perform peripheral nerve decompression or release.

Description

Nerves run from the spinal cord throughout the body through 'tunnels'. These protective tunnels are narrower in sections leading to the hands and feet, and are prone to compressing or pinching nerves. When an individual nerve is compressed, it causes symptoms only in the areas served by that nerve. With carpal tunnel syndrome, for example, a patient will have sensory complaints on the palm side of the thumb and the index and middle fingers.

Common nerve compression syndromes include carpal tunnel syndrome, cubital tunnel syndrome, tarsal tunnel syndrome and radial tunnel syndrome. Carpal tunnel syndrome is the compression of the median nerve as it passes through the carpal tunnel in the wrist. Symptoms include pain and paresthesias in the median nerve distribution. Cubital tunnel syndrome is the most common form of entrapment of the ulnar nerve caused by the compression or traction of the ulnar nerve at the elbow. The ulnar nerve runs through the passage known as the cubital tunnel just behind the elbow. Since the ulnar nerve lies directly next to the bone on the inner portion of the elbow, excessive pressure on the nerve causes numbness, tingling and pain in the elbow, forearm, hand and/or fingers leading to cubital tunnel syndrome. Tarsal tunnel syndrome is caused by the compression of the main nerve (posterior tibial nerve) that passes under the medial or inside part of the ankle. The tibial nerve follows a curved route down the back portion of the leg, to the ankle, where it turns and curls below the inside of the ankle. When the nerve is entrapped in the tarsal tunnel, swelling occurs around the nerve and the ensuing scarring of the nerve inhibits blood flow to the nerve. As the ankle joint continues to move, the nerve is further compressed and the ability of the nerve to properly function is diminished. Symptoms include burning or numbness usually at the bottom of the foot that might aggravate while standing or walking. Radial tunnel syndrome is compression of the radial nerve in the proximal forearm. Compression at the elbow may be caused by trauma, ganglia, lipomas, bone tumors, or radiocapitellar (elbow) synovitis. Symptoms include lancinating pain in the dorsum of the forearm and lateral elbow. Pain is precipitated by attempted extension of the wrist and fingers and forearm supination.

Various surgical procedures have been developed to address nerve compression syndromes. Such procedures have disadvantages, however, such as leaving large scars, causing postoperative pain, requiring relatively long recovery times, injury to adjoining nerves, and the like. Accordingly, it can be desirable to have surgical systems, methods, and devices for treating nerve compression syndromes that, among other things, address one or more of these disadvantages.

SUMMARY

Disclosed herein are systems, methods, and devices for performing endoscopic nerve release surgery. In some embodiments, a system for performing endoscopic nerve release surgery comprises: a guide apparatus, including: a handle; and a pair of spaced apart substantially parallel guides attached to the handle, the guides having opposing interior surfaces creating a space therebetween; and a knife unit having a first end, a second end and an outer surface, said outer surface configured to be received within said space between said guides; and a cannula configured to attach said second end of said knife unit to an endoscope.

According to some embodiments, the handle further comprises: an upper support, one of said pair of parallel guides affixed to said upper support; and a lower support, the other of said pair of parallel guides affixed to said lower support, said upper and lower supports disposed substantially parallel to each other. According to some embodiments, the system further comprises: an adjusting mechanism configured to adjust a distance between said upper and lower supports. According to some embodiments, the adjusting mechanism comprises a wheel having at least one screw protruding therefrom, wherein the at least one screw engages threads of a threaded aperture in the upper or lower support. According to some embodiments, the adjusting mechanism is configured to rotate in a manner that increases or decreases the distance between the upper and lower supports and in turn the distance between said parallel guides. According to some embodiments, said adjusting mechanism including at least one rod disposed between said upper and lower supports in a manner that serves to keep said upper and lower supports substantially parallel to one another. According to some embodiments, the parallel guides are substantially perpendicular to said handle. According to some embodiments, tip portions of the upper guide and lower guide are blunt to facilitate smooth insertion and passage of the parallel guides within tissues of a human body. According to some embodiments, the upper guide and the lower guide are substantially concave along their lateral axis. According to some embodiments, the upper guide and the lower guide have longitudinal slots to allow direct visualization of tissues within the human body when inserted therein. According to some embodiments, the space between the upper guide and lower guide is concave to facilitate positioning and retention of the knife unit. According to some embodiments, said knife unit further comprises: a tubular sheath extending between said first and second ends, said second end configured to attach to an endoscope; an upper limb and a lower limb extending from said first end of said tubular sheath and being substantially parallel to one another; and a blade disposed vertically in between the upper limb and the lower limb. According to some embodiments, a cutting edge of the blade is inclined relative to the longitudinal axis of the tubular sheath. According to some embodiments, distal ends of the upper limb and lower limb extend a small length beyond the blade to prevent the blade from accidental engagement with surrounding tissues within a human body. According to some embodiments, the upper limb and the lower limb comprise slots extending along their longitudinal axis providing visualization of surrounding tissues within a human body. According to some embodiments, the blade is secured vertically in between the upper limb and the lower limb by undercuts configured to engage the cutting blade and prevent accidental dislodging while operating. According to some embodiments, the tubular sheath has an aperture extending therethrough configured receive a probe head of an endoscope wherein the operating site is fully illuminated and within constant view. According to some embodiments, the cannula further comprises: a first cylindrical sheath having a first end and a second wherein the second end of the first cylindrical sheath is configured to be attached to the proximal end of an endoscope; and a second cylindrical sheath attached to the first end of the first cylindrical sheath. According to some embodiments, an external diameter of the second cylindrical sheath is approximately equal to an external diameter of the knife unit. According to some embodiments, a front end of the second cylindrical sheath of the cannula is attached to the second end of the knife unit. According to some embodiments, the cannula has a narrow cylindrical passage extending longitudinally through its length. According to some embodiments, a diameter of the cylindrical passage is configured to facilitate the insertion tube of an endoscope.

In some embodiments, a method for nerve decompression comprises: making an incision at the affected area; creating a space, with a dilator, around the fascia after identification of the nerve; inserting a guide apparatus into said space, said guide apparatus including a handle and a pair of spaced apart substantially parallel guides attached to the handle, the guides having opposing interior surfaces creating a space therebetween; creating space between said parallel guides by adjusting said guide apparatus; inserting a knife unit into said space between said parallel guides, said knife unit having a tubular sheath extending between first and second ends, said second end configured to attach to an endoscope, an upper limb and a lower limb extending from said first end of said tubular sheath and being substantially parallel to one another, and a blade disposed vertically in between the upper limb and the lower limb; and incising the nerve compressing fascia by advancing the knife unit through fascia while using an endoscope to visualize the fascia and blade of the knife unit.

According to some embodiments, the parallel guides are adjusted closer to one another before inserting the parallel guides inside the incision. According to some embodiments, the parallel guides are adjusted to a further spaced apart relation after insertion into said incision to create a space therebetween. According to some embodiments, a surgeon can directly view the fascia as being cut through a display device connected to the endoscope.

In one embodiment, a system for performing endoscopic nerve release surgery comprises a knife unit comprising a parallel upper limb and a lower limb terminating proximally at the cap of a tubular sheath. The knife unit comprises a triangular shaped surgical cutting blade disposed vertically in between the upper limb and the lower limb to facilitate the cutting of the tissue with minimal effort while passing through the fascia. Preferably the front portions of both the upper limb and lower limb extend distally to a small length beyond the cutting blade in a manner that facilitates proper positioning and engaging of the tissue to be cut. The upper limb and lower limb also comprise open slots extending longitudinally to facilitate capture, cutting and separation of the fascia while allowing the surgeon complete visualization of less routing structures and protecting the nerve and sensory surrounding nerves up above. In this embodiment, the knife unit is attached to an endoscope such that the probe head of the endoscope fits a small aperture provided on the cap of the knife unit. The strategic position of the probe head just behind the cutting blade of the knife unit provides a constant view of the operating site as the fascia is being cut and also facilitates sufficient illumination of the operating site. As the knife unit proceeds through the fascia, the cutting blade cuts the fascia in its path whereas the extended upper limb and the lower limb protect the adjoining tissue against accidental engagement with the cutting blade.

In some embodiments, a system for performing endoscopic nerve release surgery also comprises a guiding system that comprises a handle unit and a pair of adjustable parallel guides aligned perpendicular to the handle unit (or other than perpendicular in other embodiments). The parallel guides of the guiding system preferably have elongated surfaces that are configured to facilitate insertion of the knife unit into the space created by the parallel guides. The handle further comprises an upper handle (or support) and a lower handle (or support) disposed parallel to each other. An adjusting wheel having an upper screw and a lower screw is disposed in between the upper handle and the lower handle. The adjusting wheel joins the upper handle with the lower handle by rotatably engaging the threads of the upper screw inside the nut aperture on the upper handle and rotatably engaging the threads of the lower screw inside the nut aperture on the lower handle. The adjusting wheel is configured to increase or decrease the opening formed by the upper guide and the lower so that the diameter of the opening created by the parallel guides can be adjusted to a desired opening easily by the adjusting mechanism whenever required. In some embodiments, such as is shown in FIG. 5, discussed below, the adjusting wheel is positioned differently and has only one screw extending therefrom.

The parallel guides of the guiding system may further comprise an elongated upper guide attached to distal end of the upper handle and an elongated lower guide attached to distal end of the lower handle wherein the lower guide is arranged in parallel and under the upper guide. Preferably, the angle between the handles and the parallel guides is approximately 90 degrees to facilitate vertical insertion of the parallel guides inside the incision while allowing the surgeon to hold it firmly in a fixed position without interfering with other tools. The tip portions of the upper guide and lower guide are made blunt in order to facilitate smooth insertion and passage of the parallel guides through the fascia and assist them in following a predetermined path into the tissue to the operative site. In some embodiments, both the upper guide and the lower guide are substantially concave in shape along their lateral axis for better positioning of the parallel guide above the nerve or the tissue. The overall shape of the region in between the upper guide and lower guide (e.g., the shape created by opposing interior surfaces of the upper and lower guides) is in some embodiments preferably circular (or in some embodiments oval, oblong, round, or the like) in order to facilitate proper placement and prevent derailing of the endoscopic knife unit during operation. Further, in some embodiments, an exterior surface of the upper and/or lower guides is circular, arced, rounded, beveled, convex, and/or the like in shape. In some embodiments, both the upper guide and lower guide are provided with relatively long open slots along their longitudinal axis that allows, in at least some embodiments, complete and direct visualization of the tissue above and nerve underneath (for example, through the endoscope attached to the knife unit) at all times (or at some times) while performing the nerve release surgery. This is another safety feature in order to prevent iatrogenic injury to the nerve that is being decompressed. The open slots also provide better grip to the knife endoscope assembly during surgery and prevent from derailing.

While keeping the upper guide and the lower guide in the open position, the endoscope along with the knife unit can be easily slid inside the incision through the space created between the upper guide and the lower guide. As the knife unit proceeds towards the operating site using the invented guiding system, the parallel guides provide guidance to the endoscopic knife unit while cutting the fascia while working as a cannula of adjustable diameter. The parallel rods keep the upper handle and lower handle in parallel position and prevent them from undesirable movements while being operated. In some embodiments, as will be further described below, a single rod, instead of two parallel rods, is used.

After identification of the nerve at the affected area, the fascia overlying the nerve is partially released after making an incision at the operating site. Tunnelization above and below the fascia is performed through sequential dilators. Parallel guides provided on the guiding system are then introduced inside the incision, with the upper guide above the fascia and the lower guide under the fascia. In some embodiments, this is an important process in order to prevent injury to the sensory nerves that could potentially be injured during the cutting of the fascia if they are not protected. While inserting the guiding system inside the incision, the parallel guides can be kept in closed position so as to allow the insertion through a small opening of the incision. After full insertion, the parallel guides can be slowly moved apart up by rotating the adjusting wheel. The endoscopic knife unit can be inserted inside the space created between the parallel guides while allowing the knife unit to cut upon the fascia while passing through it. One advantage of the guiding system is that it facilitates the expansion of the tunnel created by the two parallel guides, after inserting inside the body. The guiding system, in some embodiments, requires a very small incision of approx. 1.5 to 2 cm be made on the body and also allows an easy and smooth adjustment of parallel guides with the help of adjusting wheel disposed in between the upper handle and lower handle.

Further, a method for nerve decompression is disclosed. The method for nerve decompression is initiated by making an incision at the affected area. A dilator of suitable size is introduced slowly into the fascia in order to create a space. The dilator creates a space sufficient for the entry of parallel guides of the guiding system inside the incision without any resistance and lifts up the superficial sensory nerves while reducing the risk of iatrogenic injury to the proximate nerves. Before insertion, the parallel guides are brought closer together by rotating the adjusting wheel of the guiding system. After the space is created, the dilator is removed and front portion of the parallel guides is inserted through the incision. After insertion, the parallel guides are moved apart slowly by rotating the adjusting wheel. At this point, the preassembled endoscopic knife unit is introduced to the operating site through the opening formed by the parallel guides of the guiding system. The surgeon can view the operating site through the video camera attached to the probe head of the endoscope and can easily adjust and position the knife unit as it passes through the fascia. The knife unit cuts and separates the fascia it passes through. The upper limb and the lower limb disposed on both the sides of the cutting blade protect the tissue against accidental cutting engagement with the blade. The parallel guides of the guiding system further serve as cannula of adjustable diameter that remains at a fixed position through the flesh. When required, the surgeon can quickly remove the knife unit attached to the endoscope and reintroduce a new knife unit without damaging the surrounding tissue. After the pressure has been released completely from the operating site, the guiding system is removed and incision is stitched.

One advantage of the invented systems is that the entire surgical process can take only a few minutes and reduces or completely diminishes the trauma and pain associated with commonly available methods and apparatuses. As the cutting blade of the endoscopic knife unit proceeds through the parallel guides of the guiding system it captures, cuts and separates the fascia in its path, while protecting the adjoining tissue against accidental engagement with the cutting blade. The surgeon can view the operating site through the video camera attached to the probe head of the endoscope and can easily adjust and position the knife unit as it passes through the fascia. Since the endoscope is positioned in between the two parallel guides the open slots on the upper guide and the lower guide prevent the knife unit from derailing as the endoscope advances towards the operating site. Hence, the undesired movement of the cutting blade, and thus the potential danger of accidental cutting of tissue other than at the desired location are avoided. The parallel guides of the guiding system further serve as a cannula of adjustable diameter wherein the surgeon can increase or decrease the diameter of the space, whenever required, while keeping it at a fixed position at the operating site. The surgeon can also quickly remove the worn out knife unit attached with the endoscope and can reintroduce a new knife unit without damaging the surrounding tissue. The systems, devices, and methods described in the present disclosure give excellent results in terms of recovery and postoperative complications.

These together with other objects of the disclosure, along with various features of novelty that characterize the inventions disclosed herein, are pointed out with particularity in the claims annexed hereto and forming a part of this disclosure. For a better understanding of the inventions disclosed herein, their operating advantages and the specific objects attained by their uses, reference should be had to the accompanying drawings and descriptive matter in which there is illustrated various embodiments.

For purposes of this summary, certain aspects, advantages, and novel features of the inventions are described herein. It is to be understood that not necessarily all such advantages may be achieved in accordance with any particular embodiment of the inventions. Thus, for example, those skilled in the art will recognize that the inventions may be embodied or carried out in a manner that achieves one advantage or group of advantages as taught herein without necessarily achieving other advantages as may be taught or suggested herein. Further, the above summary includes various embodiments, each of which includes a variety of features. It is to be understood that the disclosure of the present application is not limited to the embodiments and features presented in this summary, and various embodiments may include one, more, or all of the features disclosed herein, a combination of features from different embodiments, and/or the like.

BRIEF DESCRIPTION OF THE DRAWINGS

The foregoing and other features, aspects and advantages of the embodiments of the inventions are described in detail below with reference to the drawings of various embodiments, which are intended to illustrate and not to limit the inventions. The drawings comprise the following figures in which.

DETAILED DESCRIPTION OF THE EMBODIMENTS

Figure 1:
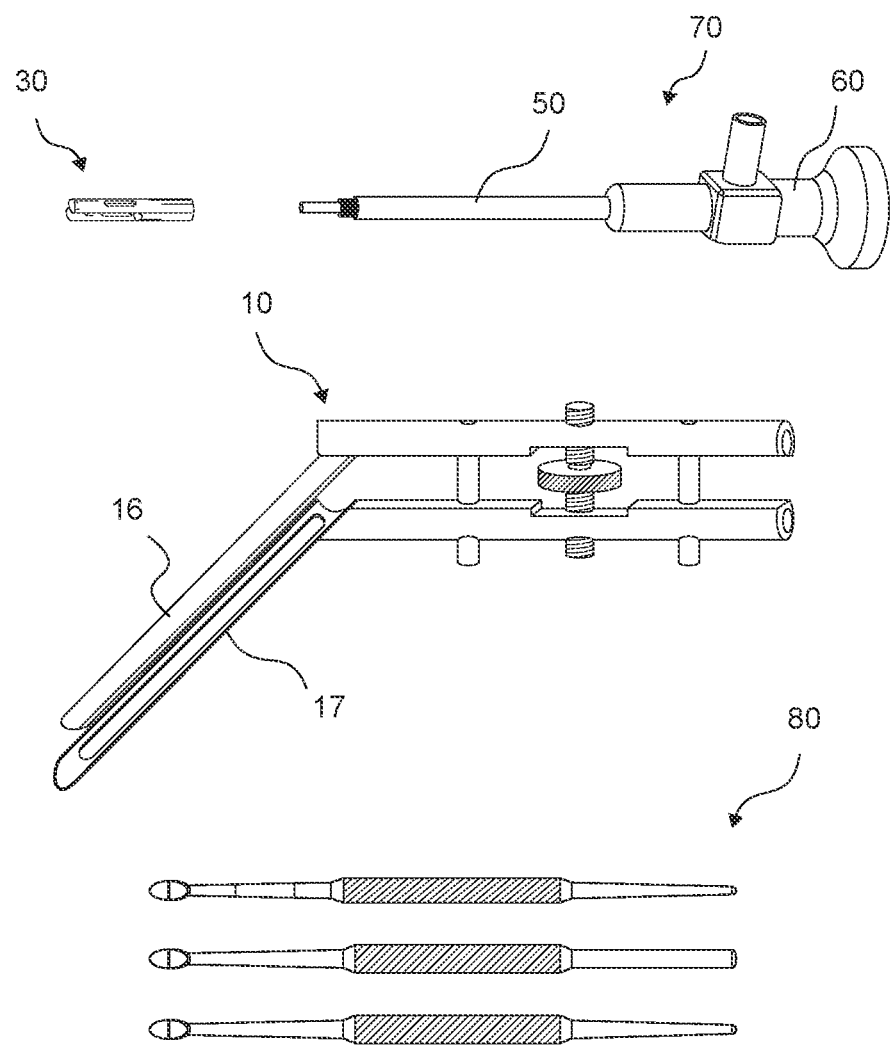
FIG. 1 illustrates a system that can preferably be included for use in nerve release surgery according to an embodiment.

Although several embodiments, examples and illustrations are disclosed below, it will be understood by those of ordinary skill in the art that the inventions described herein extend beyond the specifically disclosed embodiments, examples and illustrations, and include other uses of the inventions and obvious modifications and equivalents thereof. Embodiments of the invention are described with reference to the accompany figures, wherein like numerals refer to like elements throughout. The terminology used in the description presented herein is not intended to be interpreted in any limited or restrictive manner simply because it is being used in conjunction with a detailed description of certain specific embodiments. In addition, embodiments described herein can comprise several novel features and no single feature is solely responsible for its desirable attributes or is essential to practicing the inventions herein described.

Nerves run from the spinal cord throughout the body through 'tunnels'. These protective tunnels are narrower in sections leading to the hands and feet, and are prone to compressing or pinching nerves. Common nerve compression syndromes include carpal tunnel syndrome, cubital tunnel syndrome, tarsal tunnel syndrome and radial tunnel syndrome.

A traditional method for treating nerve compression syndromes comprises simply cutting the tissue or fascia directly above the nerve either by endoscopic methods or by other surgical methods. These methods release the pressure on the nerve trunk by the surgical excision of constricting bands or removal of constricting fibrous tissue. For example, some standard surgical procedures to treat these problems include decompression of the nerve via open carpal tunnel release (OCTR) or endoscopic methods. OCTR generally requires a large incision of approximately 6 inches, which leaves a huge scar, causes postoperative pain, requires much longer recovery time and can lead to morbidly lasting up to six months. Alternately, endoscopic methods require only a 15 mm to 25 mm skin incision, provide excellent cosmetic results and a rapid recovery, but still suffer from some disadvantages such as higher complication rates due to incomplete release of the ligament and injury to the adjoining nerves.

Though complications can arise during any operation, whether open or endoscopic, complications in open surgical techniques are likely attributable to the surgeon, whereas the majority of complications in endoscopic surgeries are method related. One of the main reasons for such complications in endoscopic procedures is the limited visualization or non-visualization of the interior nerves, as none of the existing endoscopic techniques provide adequate visualization of the operative site. Apart from this, endoscopic methods provide a limited capacity for tissue dissection during the procedure. As a result it becomes difficult to distinguish structures that are to be divided from the one that are to be preserved, since cutting in many endoscopic techniques is done according to 'all-or-none principle'. Another major problem with endoscopic methods is that a blunt-tipped tunneling forceps or a cannula is introduced distally and proximally into the space between the fascia and subcutaneous tissue and in order to widen the space, either the forceps is opened or a cannula of a larger diameter is introduced again after removing the previous one. This may accidently injure the cutaneous nerves while operation.

Various devices have been developed to facilitate and improve endoscopic procedures. One problem with many of these devices is that a cutting blade is provided directly to an operating site without any protective enclosure. As a result, the cutting blade may accidentally damage other adjoining nerves or surrounding soft tissues. Moreover, in some embodiments, an endoscope is fixed with a cutting blade, and the endoscope generally tends to slip or derail from the operating site while the surgery is being performed, which again, may seriously harm the proximate nerves or soft tissue. Further, the cannulas in many devices are tailored to a particular shape and size which does not serve the purpose for all kinds of similar surgeries related to nerve decompression. Additionally, in most of the devices, a camera and lighting on the endoscope is provided proximate to the cutting blade, providing a restricted view of the operating site.

There is, therefore, a need for a cutting blade with protective enclosure so as to prevent damage to the adjoining areas while passing through it. There is a further need for a cannula of adjustable diameter that diminishes the need of inserting cannulas of varying sizes while providing a complete visualization of the surrounding tissue during endoscopic surgery.

In this regard, the present disclosure provides, among other things, a uniquely designed knife unit and a guiding system for performing nerve decompression surgeries while allowing a complete visualization of the surrounding structures including the nerve, therefore avoiding damage to the primary peripheral nerve or surrounding sensory nerves. The inventions of the present disclosure can also be used in various types of surgical procedures in the upper or lower extremity. The disclosure also provides a novel and unique method of performing an endoscopic surgery using the invented devices.

Nerve Release Systems

Embodiments will now be described with reference to the accompanying drawings. The drawings are being used to illustrate inventive concepts and do not intend to limit the disclosure to the embodiments shown in them. Reference will now be made in detail to the description of the present subject matter, one or more examples of which are shown in the attached figures. Each example is provided to explain the subject matter and not a limitation. Although several embodiments described herein relate to cubital tunnel release, it will be understood by those skilled in the art that the methods, systems, and apparatuses disclosed herein may easily be adapted to other surgical procedures involving access to interior portions of the body through small incisions.

In an embodiment, the surgeon employs a specially designed safe and efficient knife unit that is attached to the probe head of the insertion tube of the endoscope through an adjustable cannula. An incision is made at the appropriate place where the nerve decompression has to be performed and a pathway is created by dilators for inserting the specially designed guiding system. The upper and lower guides of the guiding system serve as a cannula of adjustable diameter through which a space is created for the insertion of the endoscopic knife unit to the affected area. The endoscopic knife unit cuts apart the region of the fascia it passes through and releases the pressure on the nerve. The strategic position of the probe head of the endoscope just behind the cutting blade of the knife unit provides a constant view of the operating site as the fascia is being cut. Moreover, the open slots provided on the upper limb and the lower limb of the knife unit facilitates 360 degree visualization of the area it passes through (or in some embodiments less than 360 degrees, such as, for example, approximately 350°, 340°, 330°, 320°, 310°, 300°, 290°, 280°, 270°, 260°, 250°, 240°, 230°, 220°, 210°, 200°, 190°, or 180°). Thus, the knife unit and guiding system used in the present embodiment allows a surgeon to perform the nerve release surgery while constantly visualizing the procedure. The constant visualization of the operating site minimizes the risk of iatrogenic injury to the proximate nerves. The whole surgical procedure can take a few minutes and give excellent results in terms of recovery and postoperative complications.

The present disclosure discloses novel and unique systems, devices, and methods for performing endoscopic nerve release surgery which comprise a uniquely designed knife unit and a guiding system for performing nerve decompression surgeries while allowing a complete visualization of the surrounding structures including the nerve, therefore avoiding damage to the primary peripheral nerve or surrounding sensory nerves. Various modules of the present disclosure can also be used with various other types of surgical procedures in the upper or lower extremity.

Referring now to FIG. 1, a complete system in accordance with an embodiment is provided for use in nerve release surgery. While the system, as described herein, can be used for performing a variety of release surgeries, the release system and method will be described in conjunction with a cubital tunnel release surgery as an example of using various apparatuses in the system. Hence, such release system and method should not be limited to be used with only cubital tunnel release surgery.

The system illustrated in FIG. 1 comprises a knife unit 30 that can be used to incise the fascia surrounding the compressed nerve within the cubital tunnel in order to release the pressure. The knife unit 30 is configured to be attached to a cannula 50 by suitable fastening means (for example, threads, pins, adhesive, and/or the like). The cannula 50 is configured to be attached to a commonly available endoscope 60 or an arthroscope, which is a fiber optic scope, is introduced into a joint space through a small incision in order to carry out diagnostic and treatment procedures within the joint or space. The system also comprises a guiding system 10 that comprises a pair of adjustable parallel guides 16, 17 which are configured to be inserted inside the incision in such a way that the fascia to be cut is aligned inside the space created between the parallel guides 16, 17.

After attaching knife unit 30 and cannula 50 to the endoscope 60, the whole assembly 70 is inserted inside the incision through the space created between the two parallel guides 16, 17 of the guiding system 10. The knife unit 30 passes through the fascia and cuts and separates it as it moves through the space created between the parallel guides 16, 17 of the guiding system 10. A set of dilators 80 may also be used by the surgeon to create a space between the ulnar nerve and the forearm fascia up above and another space between the fascia and the more superficial subcutaneous tissues to facilitate entry of parallel guides 16, 17 inside the incision without any resistance (or with relatively little resistance) and lift up the superficial sensory nerves while reducing the risk of iatrogenic injury to the proximate nerves. In some embodiments, the knife unit 30 is provided sterile and is a single use item. In other embodiments, the knife unit is suitable for sterilization and reuse. The cannula 50, guiding system 10 and/or dilators 80 also can be provided non-sterile and designed for repeated sterilization in surgical setting, or can be provided as sterile single use items.

Figure 18:
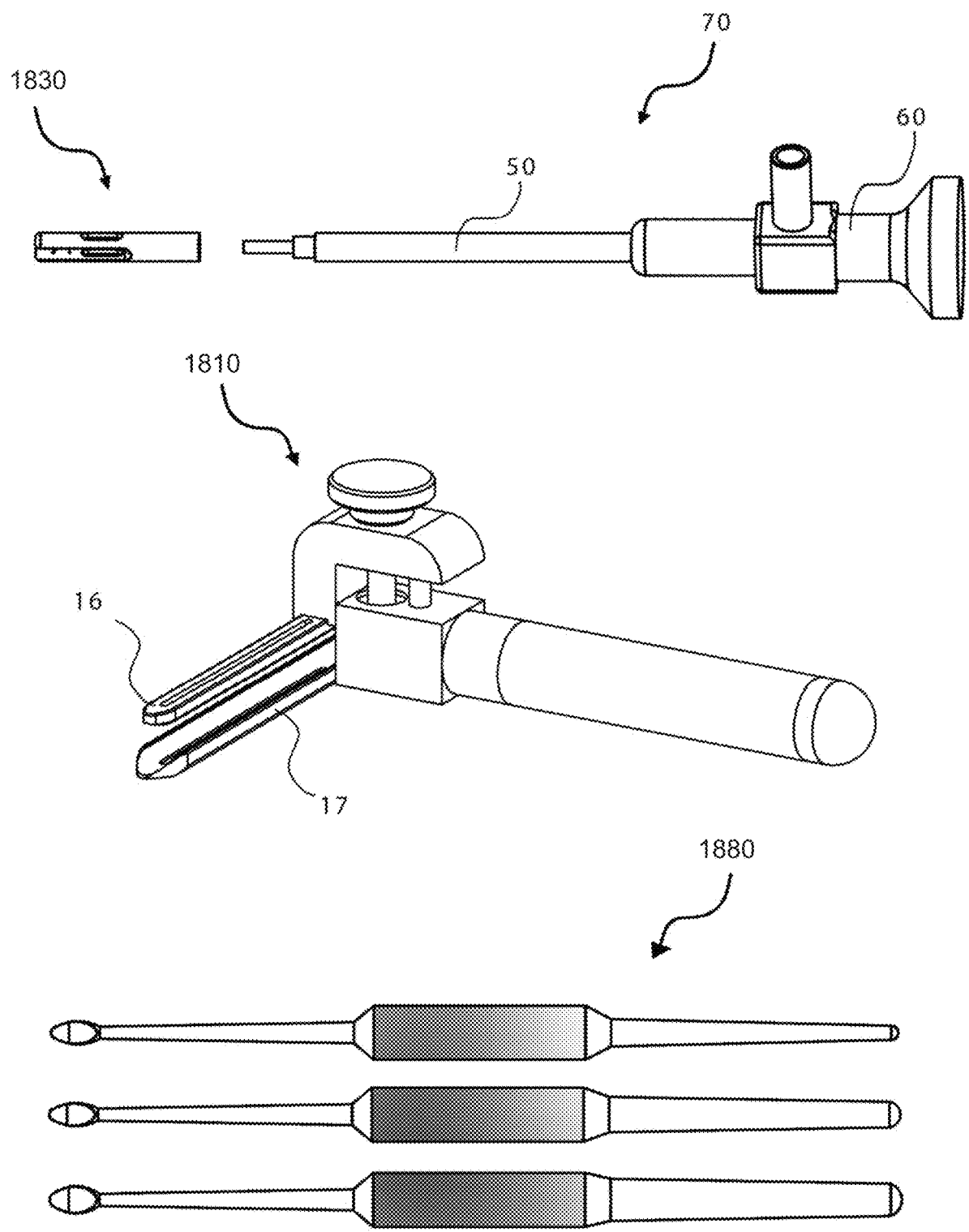
FIG. 18 illustrates another embodiment of a system that can be used in nerve release surgery.

FIG. 18 illustrates an alternative embodiment of a system for use in nerve release surgery. The system illustrated in FIG. 18 is similar to the system illustrated in FIG. 1, and like reference numbers refer to similar features. A knife unit 1830 is configured to be attached to a cannula 50. The cannula 50 is configured to be attached to an endoscope 60, to form assembly 70. The system further comprises a guiding system 1810 comprising parallel guides 16, 17, and a plurality of dilators 1880. Additional detail of this system will be given below, with reference to FIGS. 18-31.

In some embodiments, two or more components of the systems illustrated in FIGS. 1 and 18, or similar systems, may be provided as a kit for performing endoscopic nerve release surgery or other surgery. For example, one embodiment of such a surgical kit may comprise a plurality of knife units 30, 1830, and/or the like. In some embodiments, these knife units are intended to be single use and are provided in one or more packages as sterile units ready to be used during surgery. Some embodiments of a surgical kit may comprise one or more knife units 30, 1830, and/or the like, one or more guiding systems 10, 1810, and/or the like, one or more dilators 80, 1880, and/or the like, one or more cannulas 50 and/or the like, and/or one or more endoscopes 60 and/or the like.

Figure 2:
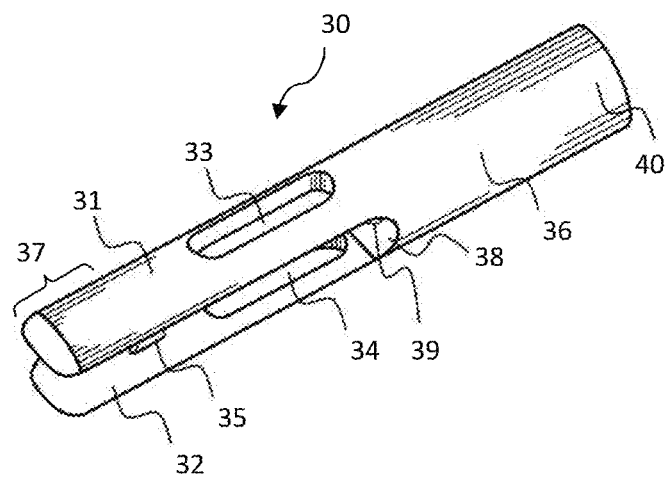
FIG. 2 illustrates a perspective view of a knife unit in accordance with one embodiment.
Figure 3:
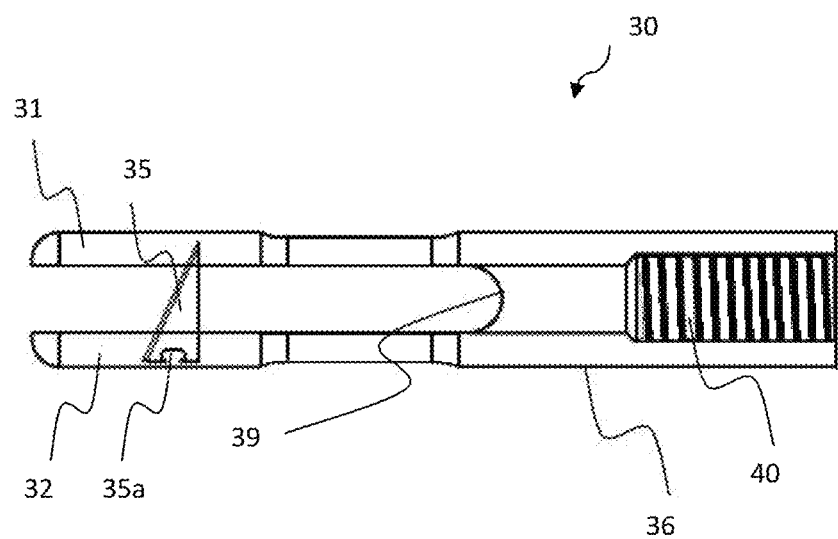
FIG. 3 illustrates a side elevation view of the knife unit of FIG. 2 in accordance with one embodiment.

Referring now to FIG. 2, a perspective view of a knife unit 30 in accordance with one embodiment is shown. In some embodiments, the knife unit 30 comprises a tubular sheath 36 having a cap 38 and an extreme end 40 extending distally wherein the extreme end 40 is configured to be attached with an endoscope through a fastening means such as a thread mechanism and the like provided internally or externally. A pair of mutually parallel upper and lower limbs 31, 32 are also provided that terminate proximally at the cap 38 of the tubular sheath 36. A surgical cutting blade 35 is disposed vertically in between the upper limb 31 and the lower limb 32 as shown in FIG. 3. The triangular shape (or slanted or angled leading edge) of the cutting blade 35 facilitates the cutting of the tissue with minimal effort while passing through the fascia. Preferably, the cutting blade 35 may be made from surgical grade stainless steel which is most suited for surgical procedures in general. The body of the knife unit 30 is made from either stainless steel, plastic or some other material suited for the purpose. In some embodiments, the front portions 37 of both, the upper limb 31 and lower limb 32 extend distally to a small length beyond the cutting blade 35. The upper limb 31 and lower limb 32 also in some embodiments comprise open slots 33 and 34 extending along their longitudinal axis to facilitate capture, cutting and separation of the fascia while allowing the surgeon complete visualization of less routing structures and protecting the nerve and sensory surrounding nerves above.

Figure 11:
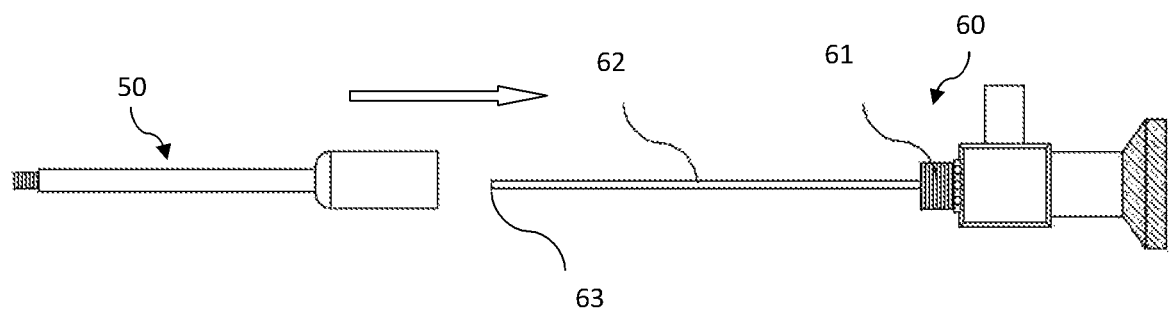
FIGS. 11a-11c illustrate views of a cannula endoscope assembly in accordance with one embodiment.
Figure 11:
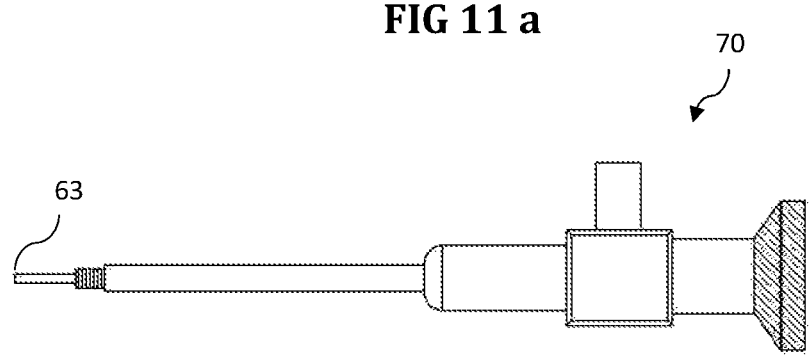
Figure 17:
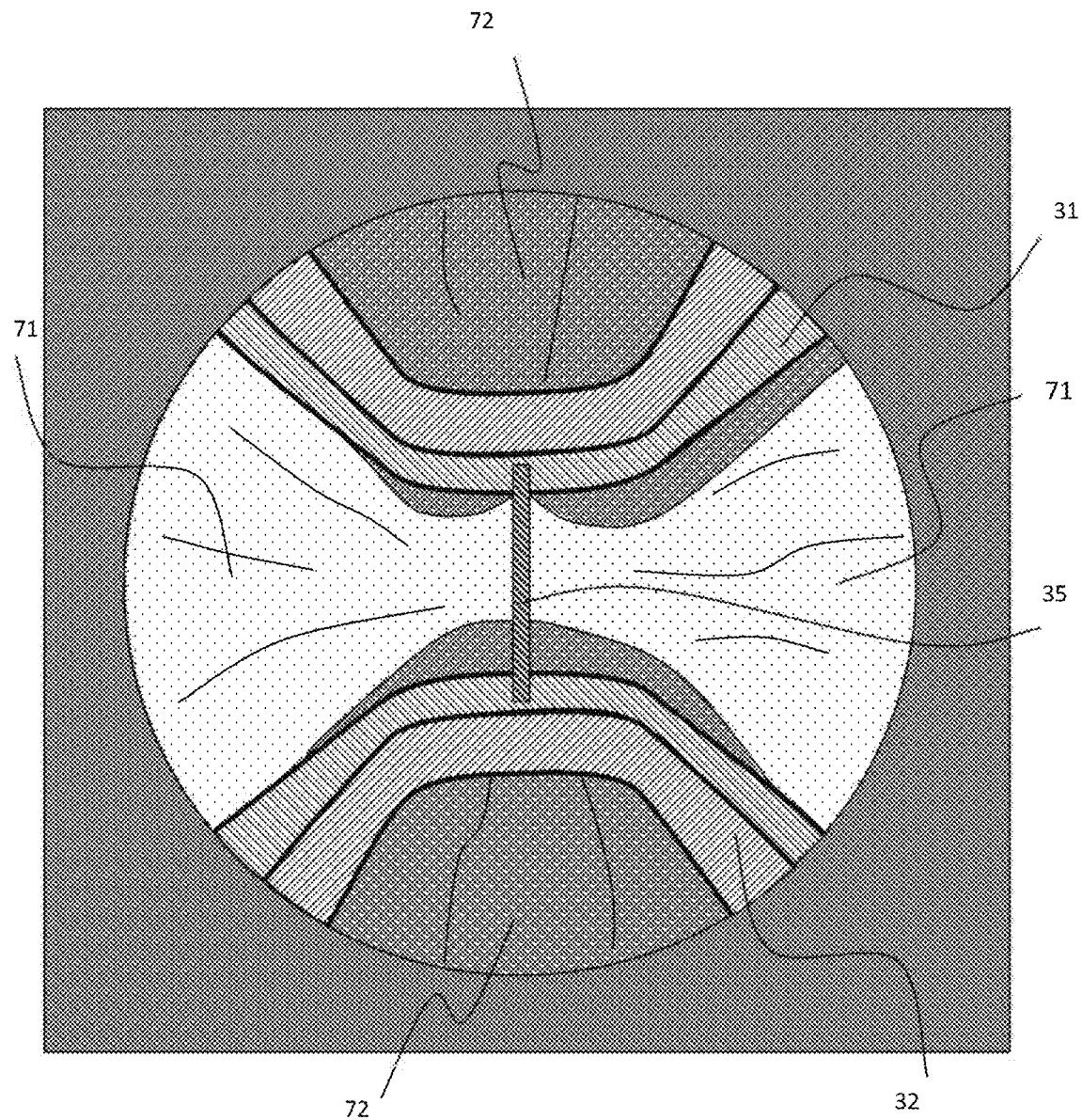
FIG. 17 illustrates a screenshot of the operating site as displayed on the display device of the endoscope during the nerve release surgery.

Referring now to FIGS. 2 and 3 in connection with FIG. 11*a*, the cap 38 has a small aperture 39 configured to dispose the image capturing device at probe head 63 of an endoscope 60 to be exposed to the operating site. The probe head 63 of endoscope 60 fits exactly (or in some embodiments, approximately) at the aperture 39 of the cap 38 when fixed inside the tubular sheath 36 via fastening means (e.g., threads, pins, adhesive, ball detent mechanism, and/or the like). The length of the tubular sheath 36 is such that when the probe head 63 of the endoscope 60 is fully inserted inside it, the probe head 63 is exposed fully to the operating site by extending forwardly through the aperture 39 of the knife unit 30 and facilitates the illumination of the operating site. The strategic position of the probe head 63 just behind the cutting blade 35 of the knife unit 30 provides a constant view of the operating site as the fascia is being cut and also facilitates sufficient illumination of the operating site. In some embodiments, the blade 35 is approximately aligned with a central axis of the aperture 39, such that the blade 35 will appear approximately in the center of the image captured by the endoscope, as shown in FIG. 17. The outer diameter of the knife unit 30 is suitable for insertion into the parallel guides 16, 17 or may be chosen according to requirement based upon the area of to be operated upon. In order to perform the surgery using knife unit 30, the knife unit 30 is attached with endoscope and can be either inserted inside the space created between the parallel guides 16, 17 of the guiding system 10 or can be used independently as well without using guiding system 10. The size and shape of the knife unit 30 can be modified as per requirement. The knife unit 30 can be provided in a sterile packaging whereas the rest of the instrumentation can be provided in a tray that can be sterilized.

Figure 4:
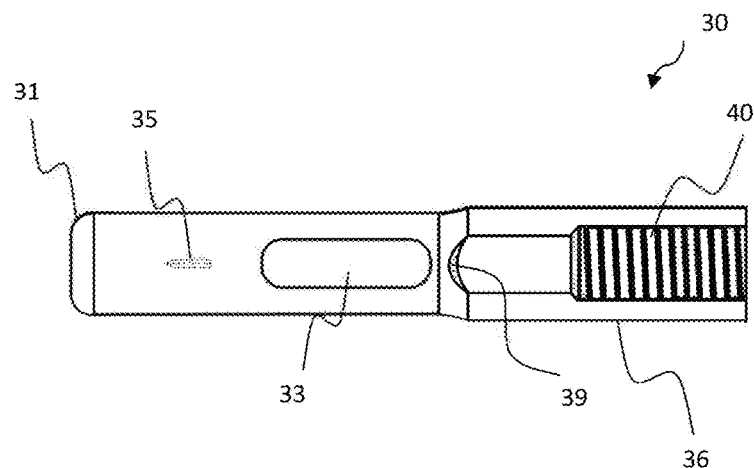
FIG. 4 illustrates a top elevation view of the knife unit of FIG. 2 in accordance with one embodiment.

Referring now to FIG. 3 and FIG. 4, these figures illustrate the side and top elevation view respectively of the knife unit 30 in accordance with one embodiment. The cutting blade 35 is disposed vertically in between upper limb 31 and the lower limb 32 of the knife unit 30. The sharp edge of the cutting blade 35 faces the front end of the knife unit 30, so that it can cut the fascia while passing through it. The cutting blade 35 is secured in between the upper limb 31 and the lower limb 32 by undercuts, slots, or grooves 35*a* (or other suitable retention means) to prevent accidental dislodging of the blade while operating. The upper limb 31 and the lower limb 32 allow the capture, cutting and separation of the fascia while allowing the surgeon complete visualization (through open slots 33 and 34 on the knife unit 30 and the open slots 18*a* and 18 on the parallel guides 16,17 of the guiding system 10) of less routing structures. The upper limb 31 and lower limb 32 also protect the adjoining tissue against accidental engagement with the cutting blade 35 and also protect nerve and sensory surrounding nerves up above. As the knife unit 30 proceeds through the fascia, the cutting blade 35 cuts the fascia in its path whereas the extended upper limb 31 and the lower limb 32 protect the adjoining tissue against accidental engagement with the cutting blade 35.

Figure 19:
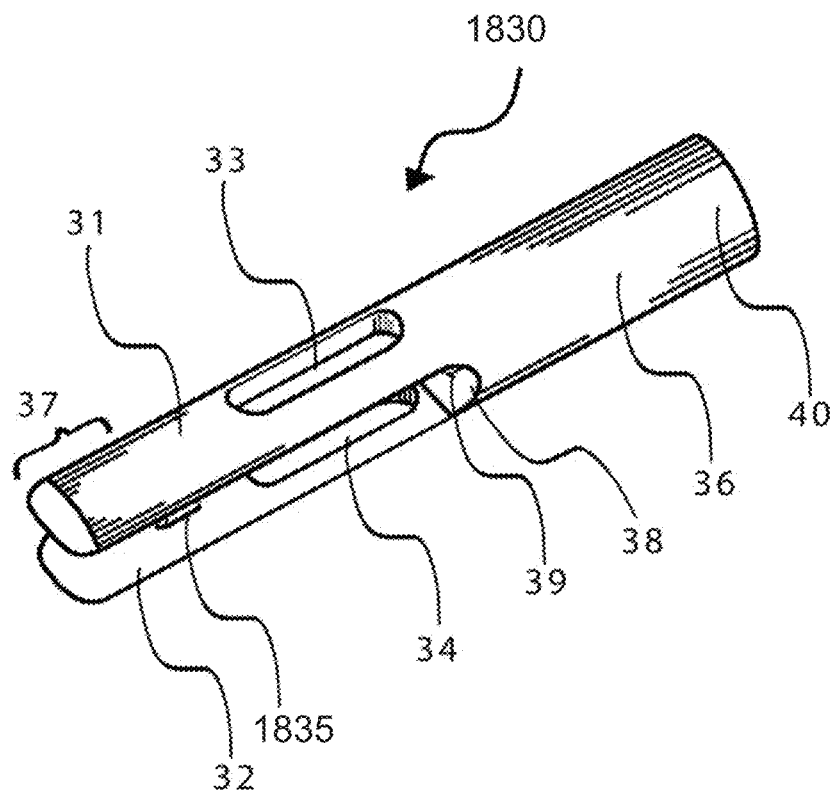
FIG. 19 illustrates a perspective view of another embodiment of a knife unit.
Figure 20:
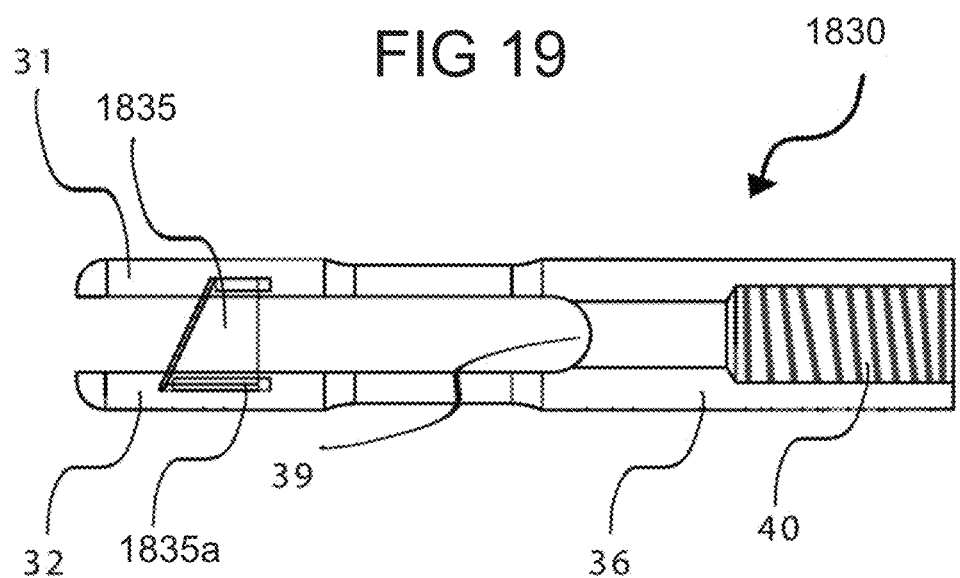
FIG. 20 illustrates a side elevation view of the knife unit of FIG. 19 in accordance with one embodiment.
Figure 21:
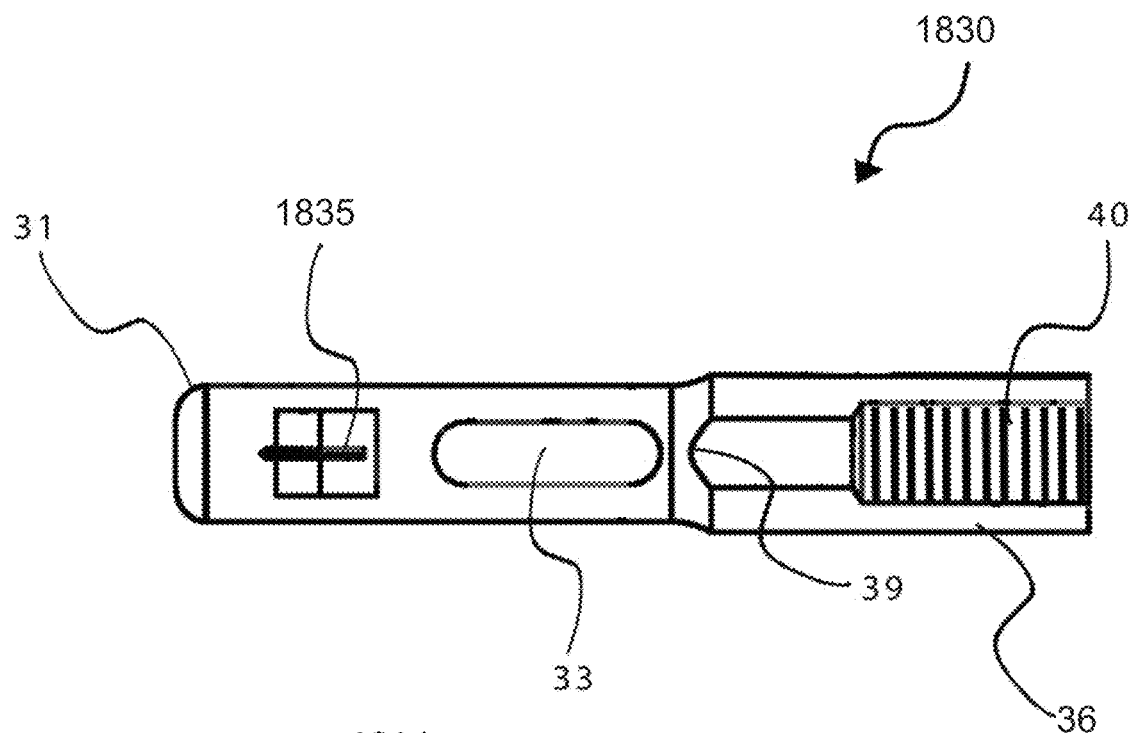
FIG. 21 illustrates a top elevation view of the knife unit of FIG. 19 in accordance with one embodiment.

FIGS. 19-21 illustrate perspective, side, and top views, respectively, of the knife unit 1830, which is similar in many respects to the knife unit 30 of FIGS. 2-4, and like or the same reference numbers are used to refer to similar or the same features. Once difference is that the knife 1835 of the knife unit 1830 comprises a trapezoidal shape instead of a triangular shape. The additional length in the longitudinal direction of knife 1835 can help to stabilize and/or retain the knife 1835. Corresponding slots, groove, or undercuts 1835a help to position and/or retain the knife 1835 with respect to upper and lower arms 31, 32.

Figure 5:
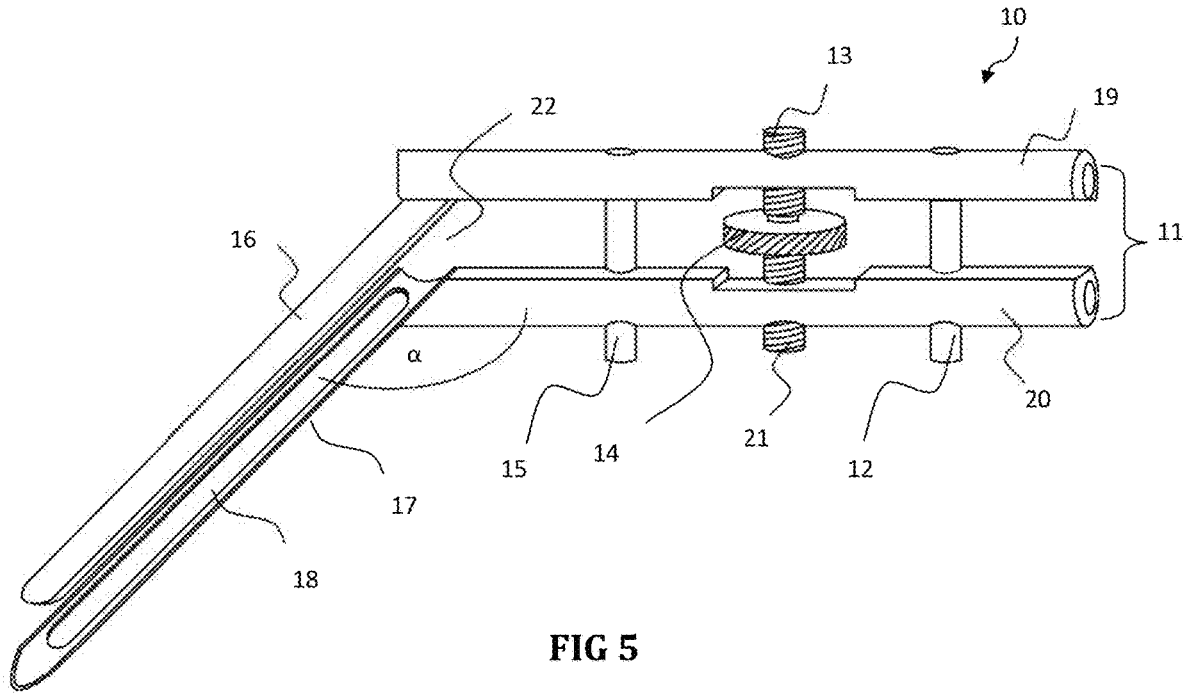
FIG. 5 illustrates a perspective view of a guiding system for use in nerve release surgery in accordance with one embodiment.

Referring now to FIG. 5, FIG. 5 illustrates a perspective view of the guiding system 10 for use in nerve release surgery in accordance with one embodiment. The figure illustrates a guiding system 10 which is part of the complete system and can be used in a variety of procedures in both upper and lower extremity. The guiding system 10 will be described with reference to cubital tunnel syndrome for the purpose of illustration. The guiding system 10 comprises generally a handle unit 11 and a pair of parallel guides 16, 17 aligned perpendicular to the handle unit 11. The parallel guides 16, 17 have elongated surface and are configured to facilitate insertion of the endoscopic knife unit 30 inside the incision by creating a space between the parallel guides 16, 17.

Figure 7:
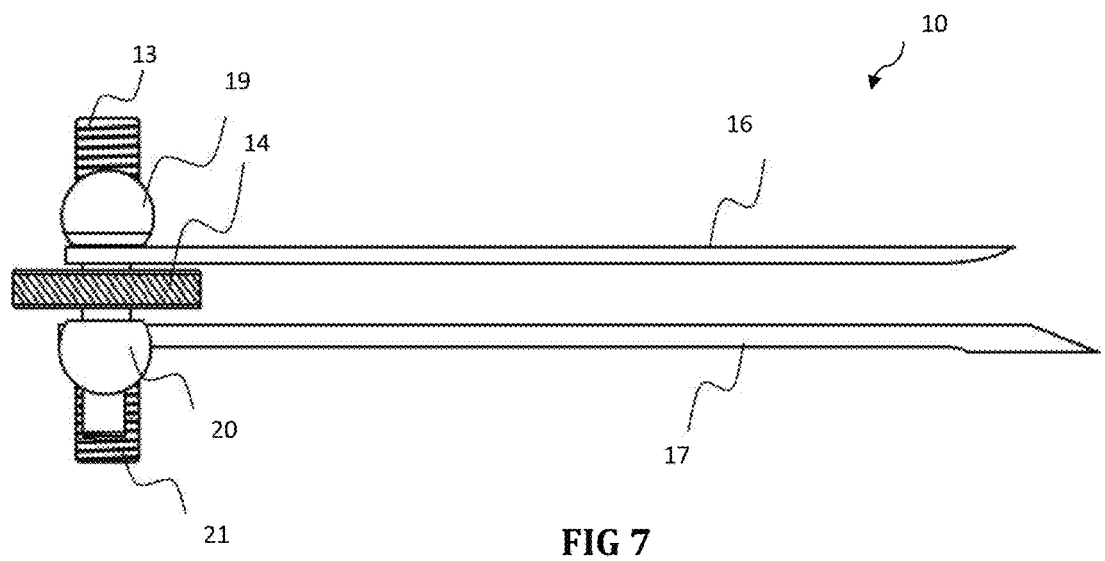
FIG. 7 illustrates a side elevation view of the guiding system of FIG. 5 with parallel guides in an open position in accordance with one embodiment.

Although in this embodiment and other embodiments disclosed herein, the upper and lower guides 16, 17 are described as being preferably parallel, in some embodiments, the upper and lower guides may not necessarily be completely parallel, and/or may be able to be become nonparallel during use of the device, such as through elastic bending, some amount of play in the guide device (for example, due to manufacturing tolerances), and/or the like. For example, with reference to FIG. 7, which illustrates the upper and lower guides 16, 17 in a parallel configuration, in some embodiments, the distal ends of the guides, which are the right ends as shown in FIG. 7, may be caused to move toward (or away from) each other when inserting the upper and lower guides into the surgical site, due to body tissue pressing against the interior and/or exterior surfaces of the upper and lower guides 16, 17. In some embodiments, the structural design of the handle assembly and/or the cross sectional shape of the guides may reduce or eliminate this movement away from parallel when the tool is being inserted. For example, making the guides a shape other than flat, such as the circular or arced shape of the lower guide 17 shown in FIG. 8, may help to stiffen the guides and/or provide additional bending resistance or rigidity. In some embodiments, the upper and lower guides are completely, substantially, or approximately parallel to one another in a resting position, or when the guide unit is not in use. In other words, an angle between the two guides is exactly, substantially, or approximately 0°. In some embodiments, however, the angle between the upper and lower guides in the resting state, such as when the tool is not yet being inserted into the surgical site, may be other than 0°. This may be beneficial, for example, to compensate for an expected or anticipated amount of movement or flexure of the upper and/or lower guide and/or the handle when inserting the guides into the surgical site. For example, this nominal angle between the guides may be in some embodiments exactly, approximately, no more than, or no less than, −5°, −4°, −3°, −2°, −1°, −0.75°, −0.5°, −0.25°, 0.25°, 0.5°, 0.75°, 1°, 2°, 3°, 4°, or 5°.

In various embodiments, an overall length of the upper and lower guides 16, 17 may vary. In general, the longer the guides, the more potential there is for bending inward and/or out word of the distal tips of the upper and lower guides when inserting the upper and lower guides into the surgical site. Accordingly, in some embodiments, a guiding system having longer upper and/or lower guides may comprise a stiffer cross-sectional design of the guides than a similar guiding system that has shorter upper and lower guides. In some embodiments, a length of the upper and/or lower guides, meaning a distance from the distal tips of the guides to the corresponding upper or lower support, is exactly, approximately, no more than, or no less than 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, or 30 cm. In some embodiments, one of the upper or lower guides comprises a different length than the other and or the distal tip of that guide extends further than the other. This can be seen, for example, in FIG. 7, where the distal end of the lower guide 17 extends further than the distal end of the upper guides 16. This configuration can be advantageous, such as, for example, to enable a smaller profile at the distal end for easier insertion into the surgical site. Further, various embodiments may comprise various ranges of adjustability of the distance between the upper and lower guides. For example, with reference to FIG. 7, the vertical distance from the uppermost surface of the upper guide 16 to the lowermost surface of the lower guide 17 may in some embodiments be exactly, approximately, no more than, or no less than 1 mm, 2 mm, 3 mm, 4 mm, 5 mm, 6 mm, 7 mm, 8 mm, 9 mm, or 10 mm at the closest and/or closed position. In some embodiments, this vertical distance across the guides in the club closed or closest position is reduced or minimized by enabling at least part of one of the guides to be nested within at least part of the other guide. For example, in some embodiments, the lower guide may comprise an at least partially concave shape within which a portion of the upper guide may fit in the closed position. Further, in some embodiments, this vertical distance from the uppermost surface of the upper guide 16 to the lowermost surface of the lower guide 17 may in some embodiments be exactly, approximately, no more than, or no less than 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm at the furthest and/or fully open position.

It should be noted that, although various embodiments disclosed herein describe an adjustable cannula with reference to two guides, namely an upper guide 16 and lower guide 17, various embodiments may comprise more than two guides used to create such an adjustable cannula. For example, some embodiments may comprise three, four, or more guides that expand and contract radially using a cam mechanism, linkage mechanism, and/or the like to alter the size of the adjustable cannula of the guiding system.

Figure 6:
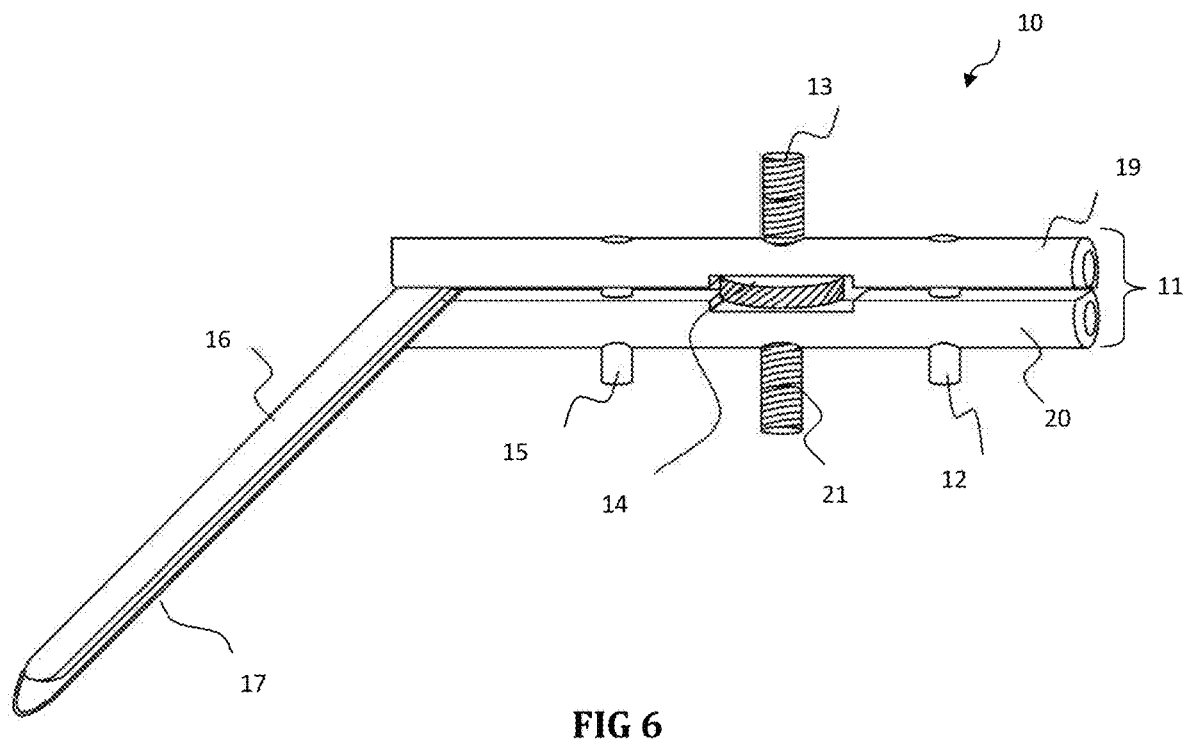
FIG. 6 illustrates a perspective view of the guiding system of FIG. 5 with parallel guides in a closed position in accordance with one embodiment.
Figure 8:
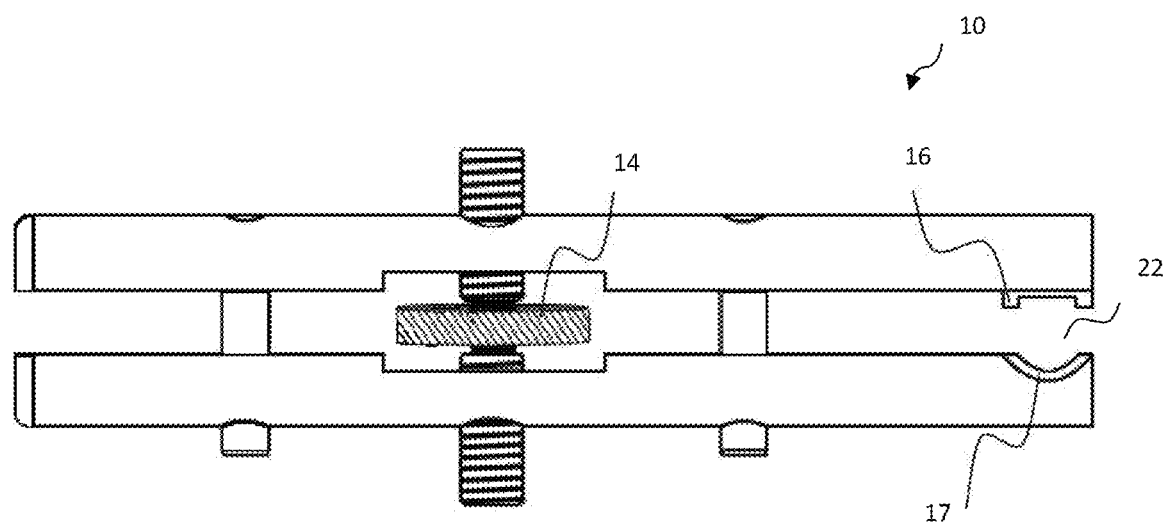
FIG. 8 illustrates a rear elevation view of the guiding system of FIG. 5 with parallel guides in the open position in accordance with one embodiment.

The handle unit 11 comprises an upper handle 19 and a lower handle 20 disposed parallel to each other. In some embodiments, the upper and lower handles are referred to as upper and lower supports. An adjusting wheel 14 having an upper screw 13 and a lower screw 21 is disposed in between the upper handle 19 and lower handle 20. The adjusting wheel 14 joins the upper handle 19 with the lower handle 20 by rotatably engaging the threads of the upper screw 13 inside the nut aperture on the upper handle 19 and rotatably engaging the threads of the lower screw 21 inside the nut aperture on the lower handle 20. The parallel guides 16,17 further comprise an elongated upper guide 16 attached to distal end of the upper handle 19 and an elongated lower guide 17 attached to distal end of the lower handle 20 wherein the lower guide 17 is arranged in parallel and under the upper guide 16. Preferably, the angle α between the handles 19, 20 and the parallel guides 16, 17 is approximately 90 degrees to facilitate vertical insertion of the parallel guides 16, 17 inside the incision and to hold the guiding system firmly in fixed position without interfering with other tools. The tip portions of the upper guide 16 and lower guide 17 are made blunt in order to facilitate smooth insertion and passage of the parallel guides 16,17 through the fascia and assist them in following a predetermined path into the tissue to the operative site. Both, the upper guide 16 and the lower guide 17 are substantially concave in shape along their lateral axis for better positioning of the parallel guides 16, 17 above the nerve or tissue. The overall shape of the region 22 in between the upper guide 16 and lower guide 17 (e.g., the shape created by opposing interior surfaces of the upper and lower guides) is preferably circular (but may be other shapes, such as, for example, oval, oblong, round, or the like) in order to facilitate proper placement and prevent derailing of the endoscopic knife unit 30 (as shown in FIG. 2) during operation. Further, in some embodiments, an exterior surface of the upper and/or lower guides is circular, arced, rounded, beveled, convex, and/or the like in shape. For example, as can be seen in FIGS. 6 and 8, the bottom, exterior, or undersurface of the lower guide 17 is circular, arced, or convex in shape, which can be beneficial to, among other things, facilitate introduction of the guide over the ulnar nerve, which is also circular or rounded in shape. In some embodiments, one or more of the guides comprises an external shape substantially similar to or configured to substantially conform to a shape of the ulnar nerve or other nerve.

In this embodiment, the lower guide 17 comprises a long open slot 18, along its longitudinal axis. In some embodiments, the upper guide 16 comprises a similar slot. These slots allow, in at least some embodiments, complete and direct visualization of the tissue above and nerve underneath (through the endoscope disposed on the knife unit 30), at all times while performing the nerve release surgery. This is another safety feature in order to prevent iatrogenic injury of the nerve that is being decompressed. The open slots 18 also provide better grip to the endoscopic knife unit 30 during surgery and prevent them from derailing. While keeping the upper guide 16 and the lower guide 17 in open position, the endoscopic knife unit 30 can be easily slid inside through the space created between the upper guide 16 and the lower guide 17. As the knife unit 30 proceeds towards the operating site using the invented guiding system, the parallel guides 16, 17 provide guidance to the endoscopic knife unit 30 while working as a cannula of adjustable diameter. The parallel rods 12, 15 keep the upper handle 19 and lower handle 20 in parallel position and prevent them from undesirable movements while being operated. In some embodiments, the length of the slot 18 in one or more of the guides comprises at least 75%, 80%, 85%, 90%, or 95% of the overall length of the guide (meaning the length of the guide from the distal tip of the guide to the corresponding upper or lower support).

The adjusting wheel 14 is configured to increase or decrease the opening 22 formed by the upper guide 16 and the lower guide 17, by rotation operation so that the diameter of the opening 22 created by the parallel guides 16, 17 can be adjusted to a desirable opening easily by screw mechanism using the adjusting wheel 14 whenever required. The orientation of threads on the upper screw 13 and the lower screw 21 are such that when the adjusting wheel 14 is rotated in one direction, both the upper handle 19 and the lower handle 20, move in opposite direction. Hence, when it is desired to create a space between the upper guide 16 and the lower guide 17 (e.g. after inserting them inside the incision), the adjusting wheel 14 is rotated in one direction so as to move the parallel guides 16, 17 apart from each other. Whereas the adjusting wheel 14 may be rotated in opposite direction in order to bring the upper guide 16 and lower guide 17, closer to each other (e.g. during the insertion of the parallel guides 16, 17 inside the body). A pair of mutually parallel rods 12 & 15 is disposed vertically on the upper handle 19 and disposed inside the cavities on the lower handle 20 configured to slidably receive the parallel rods 12 & 15 whereby keeping the upper handle 19 and the lower handle 20 parallel to each other and prevent them from undesirable movements while being operated.

After identification of the ulnar nerve, the fascia overlying the nerve is partially released after making sufficient incision at the operating site. Tunnelization above and below the fascia is performed through sequential dilators 80 (FIG. 1). Parallel guides 16, 17 provided on the guiding system 10 are then introduced inside the incision, with the upper guide 16 above the fascia and the lower guide 17 under the fascia. In some embodiments, this is an important process in order to prevent injury to the sensory nerves that could potentially be injured during the cutting of the fascia if they are not protected. While inserting the guiding system 10 inside the incision, the parallel guides 16, 17 can be kept in closed position so as to allow the insertion through a small opening of the incision. After full insertion, the parallel guides 16, 17 can be slowly moved apart up by rotating the adjusting wheel 14. The endoscopic knife unit 30 (FIG. 2) can be inserted inside the space created in between parallel guides 16, 17 while allowing the endoscopic knife unit 30 (FIG. 2) to cut upon the fascia while passing through it. One advantage of the guiding system 10 is that it facilitates the expansion of the tunnel created by the parallel guides 16, 17, after inserting inside the body. The guiding system 10, in some embodiments, requires a very small incision of approx. 1.5 to 2 cm to be made on the body and also allows an easy and smooth adjustment of parallel guides 16, 17 with the help of adjusting wheel 14 disposed in between the upper handle 19 and lower handle 20.

Referring now to FIG. 6, FIG. 6 illustrates a perspective view of the guiding system 10 with parallel guides 16, 17 in closed position in accordance with one embodiment. When the adjusting wheel 14 is rotated in opposite direction (as while opening the parallel guides 16, 17), the upper guide 16 and the lower guide 17 guide are brought closer due to screw mechanism provided by the upper screw 13 and the lower screw 21. The closed position of the parallel guides 16, 17 allows an easy insertion of the apparatus inside the body through a small incision. Conventionally, for smaller incision, a cannula of small diameter has to be inserted which again has to be withdrawn when it is required to place a cannula of larger diameter. This makes the procedure cumbersome while causing serious damage to the surrounding nerves as well. Using the guiding system 10, as described above, the desirability of cannulas of varying size is completely diminished since the diameter of the tunnel created by the guiding system 10 can be adjusted to a desirable diameter easily by the screw mechanism using adjusting wheel 14, whenever required. As described above, the apparatus or tool can be designed to be used with various other procedures as well. The apparatus specifically provides minimal invasive surgery through smaller incision.

Referring now to FIG. 7, FIG. 7 illustrates a side elevation view of the guiding system 10 with parallel guides 16, 17 in open position in accordance with one embodiment. The figure shows the open position of the parallel guides 16, 17 through which the endoscopic knife unit 30 (FIG. 2) can be inserted. The blunt ends of the parallel guides 16, 17 allow for easy insertion and passage through the fascia and assist them in following a predetermined path into the tissue to the operative site. The diameter of the predetermined path may be increased or decreased by rotating the adjusting wheel 14 as described above.

Referring now to FIG. 8, FIG. 8 illustrates a rear elevation view of the guiding system with parallel guides in open position in accordance with one embodiment. The endoscopic knife unit 30 can be inserted from the region marked as 22 in the figure after opening the parallel guides 16, 17 by rotating the adjusting wheel 14.

Figure 22:
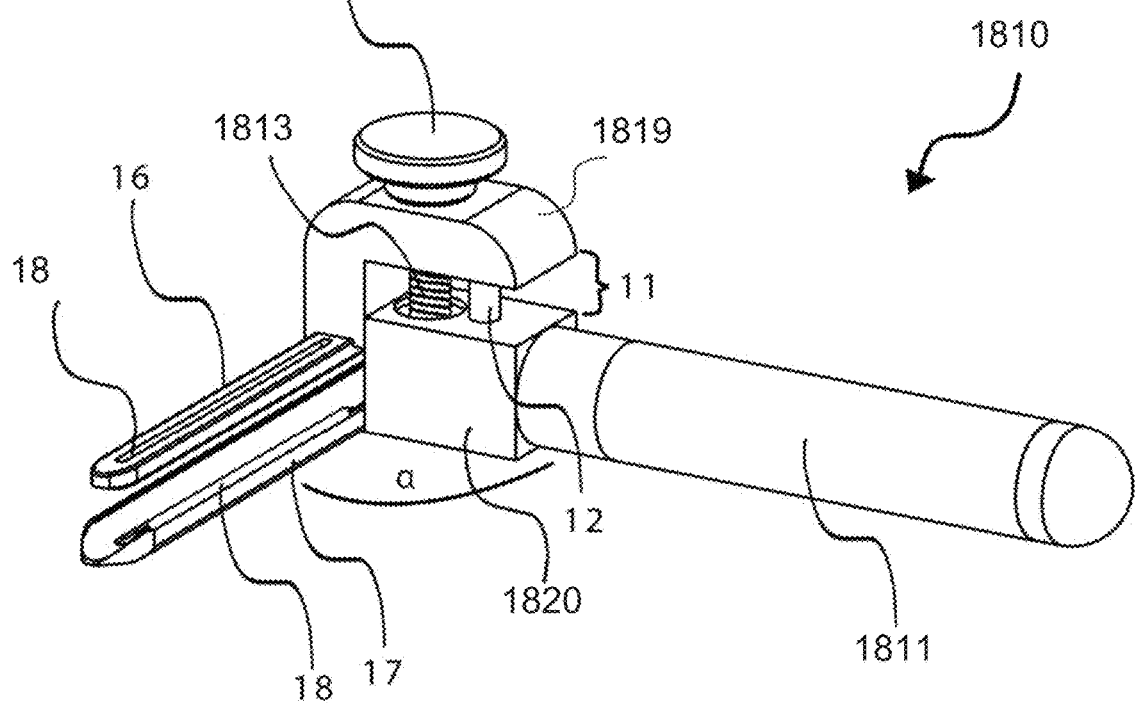
FIG. 22 illustrates a perspective view of another embodiment of a guiding system for use in nerve release surgery.
Figure 23:
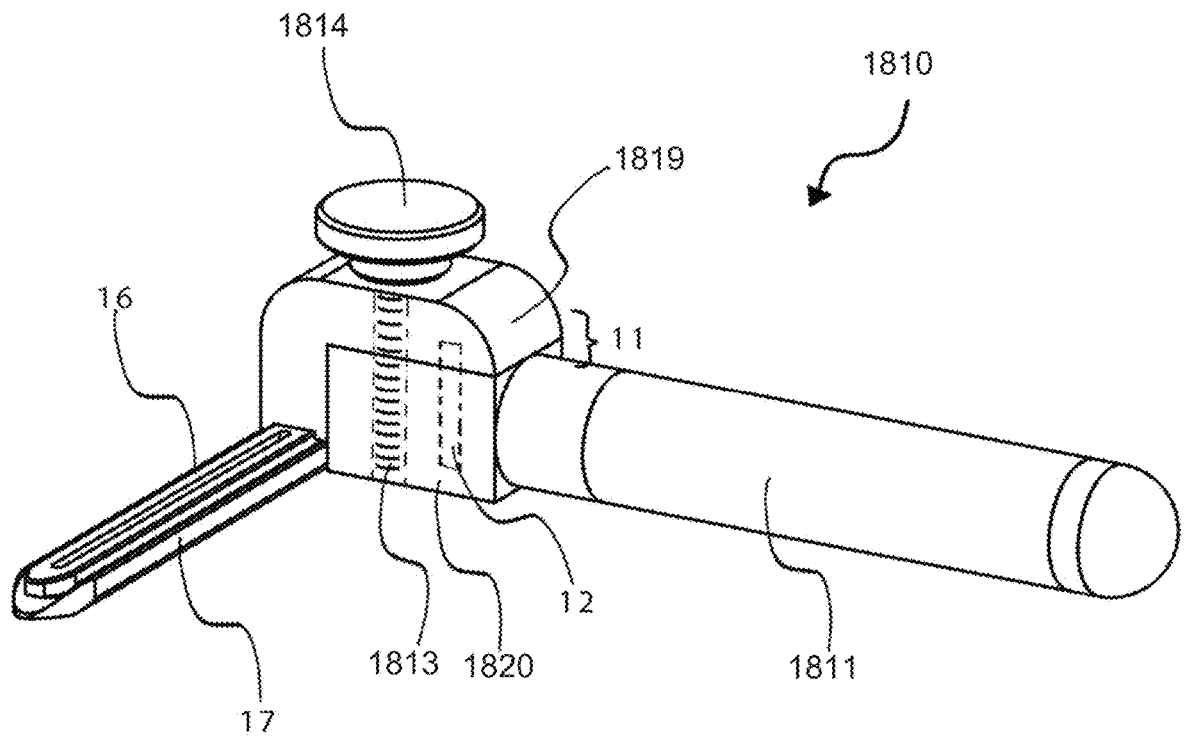
FIG. 23 illustrates a perspective view of the guiding system of FIG. 22 with parallel guides in a closed position in accordance with one embodiment.
Figure 24:
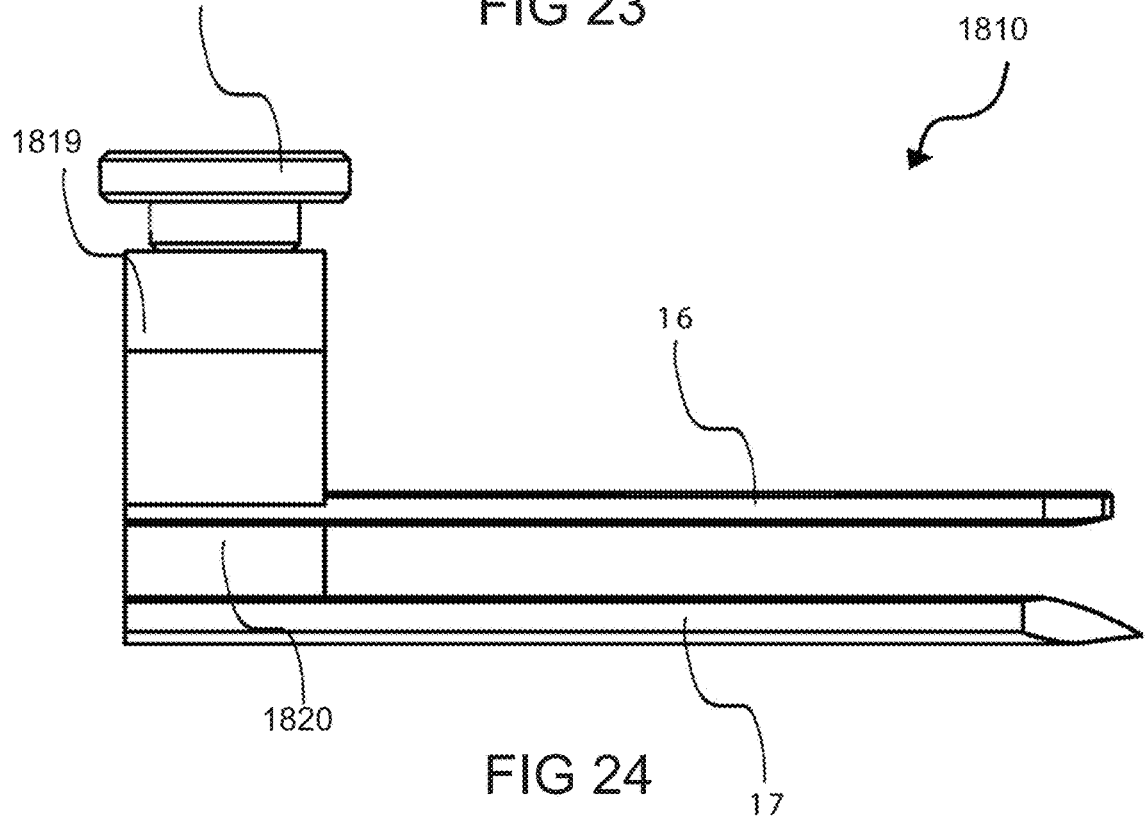
FIG. 24 illustrates a side elevation view of the guiding system of FIG. 22 with parallel guides in an open position in accordance with one embodiment.
Figure 25:
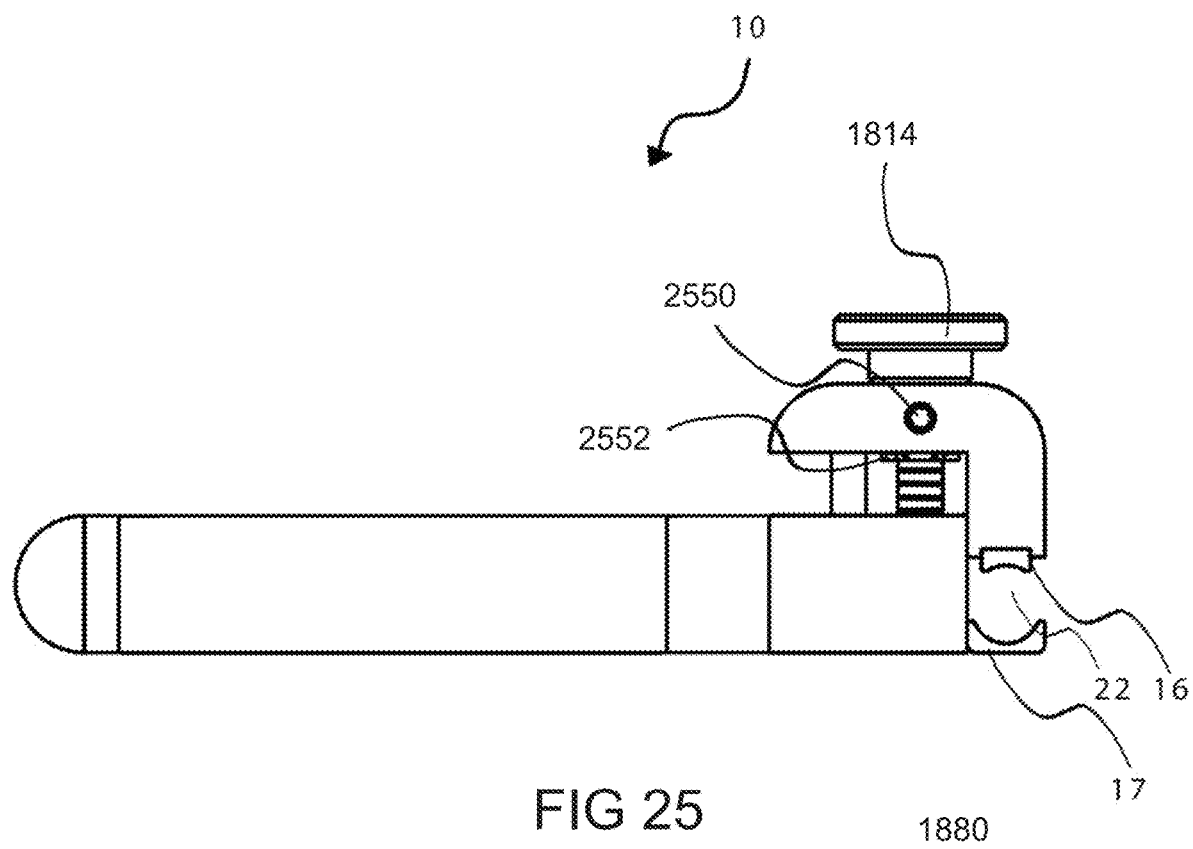
FIG. 25 illustrates a rear elevation view of the guiding system of FIG. 22 with parallel guides in the open position in accordance with one embodiment.

FIGS. 22-25 illustrate an alternative embodiment of a guiding system 1810, which is similar in function to the guiding system 10 of FIGS. 5-8. The same or similar reference numbers are used to refer to the same or similar features. FIG. 22 illustrates a perspective view of the guiding system 1810 with its parallel guides 16, 17 in an open position. FIG. 23 illustrates a perspective view of the guiding system 1810 with its parallel guides 16, 17 in a closed position. FIG. 24 illustrates a side elevation view of the guiding system 1810 with parallel guides 16, 17 in the open position. FIG. 25 illustrates a rear elevation view of the guiding system 1810 with parallel guides 16, 17 in the open position.

The guiding system 1810 is similar to the guiding system 10, with a main difference being that the guiding system 1810 comprises a unitary handle 1811, instead of a two-piece handle 11. To enable the guides 16, 17 to move relative to one another, the guiding system 1810 comprises a lower support 1820 affixed to or forming a part of the handle 1811, and a moveable upper support 1819. An adjusting wheel 1814 is coupled to a screw 1813, which passes through the upper support 1819 and engages a threaded portion of the lower support 1820. Rotation of the adjusting wheel 1814 causes the upper support 1819 to move closer to or further from the lower support 1820, depending on the direction the wheel 1814 is turned. Rod 12 acts as an anti-rotate or stabilization device to keep the guides 16, 17 in a substantially parallel configuration as the wheel 1814 is turned. With reference to FIG. 25, the guiding system 1810 further comprise a set screw 2550 and a retaining clip 2552. One or both of these features can be used to prevent loosening of the main screw 13 and/or to hold the main screw 13 in a particular position.

Although the embodiments illustrated in FIGS. 5 and 22 both illustrate embodiments of guiding systems that utilize an adjusting wheel and screw or screws to adjust a distance between the upper and lower guides 16, 17, various other mechanical or electromechanical mechanisms may be used to adjust to the distance between the upper and lower guides. In some embodiments, different stabilizing and/or anti-rotation features may be used than the rods 12, 15, such as rectangular rods or guides, mating surfaces of the upper and lower supports that slide against each other, more than two guiding rods, such as three or four guiding rods, and/or the like. In some embodiments, the guiding system may utilize a scissor type mechanism to vary the distance between the upper and lower guides 16, 17, instead of or in combination with one or more screws. In some embodiments, the guiding system may utilize a cam, lead screw, ball screw, or other feature or features that transform motion of a user input, such as an adjustment wheel, lever, knob, and/or the like, into movement of the upper and lower guides toward or away from each other. Further, in some embodiments, one or more electromechanical mechanisms are utilized, such as a motor that drives a screw or other mechanism to cause the upper and lower guides to move relative to one another in response to an electrical input. In some embodiments, a spring or other mechanism is used to preload or bias the upper and lower guides in the outward and/or inward direction with respect to each other. This may, for example, make it easier for a user to adjust the upper and lower guides in one direction than the other direction, and/or may provide some assistance to the user when opening or closing the upper and lower guides against the pressure of body tissue. In some embodiments, a spring or other preload device, a set screw, a locking pawl, a ball detent mechanism, and/or the like may be utilized to help retain the upper and lower guides in a specific relative position without requiring the user to manually maintain the upper and lower guides in that relative position. In some embodiments, a screw used to adjust the distance between the guides, such as the screws 13, 21, and 1813 shown in FIGS. 5 and 22, is designed to be self-locking or non-backdrivable, meaning the lead of the screw is shallow enough that the screw will not be back driven by pressure applied to the upper and/or lower guides.

Figure 9:
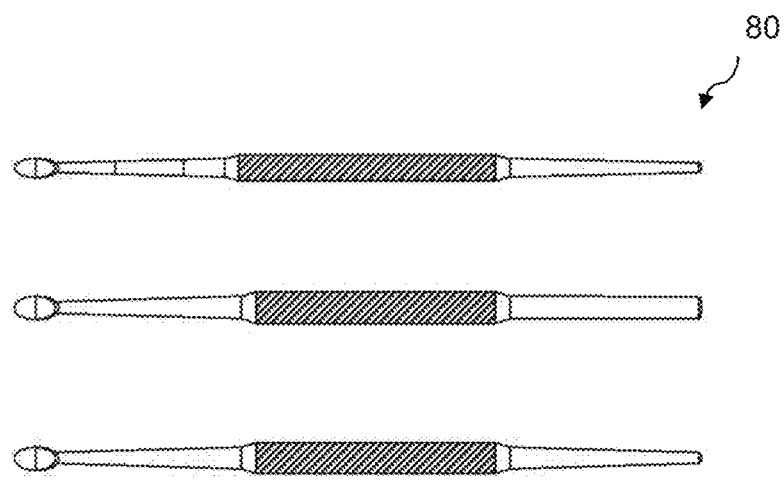
FIG. 9 illustrates an orthogonal view of embodiments of dilators used in conjunction with an embodiment.
Figure 26:
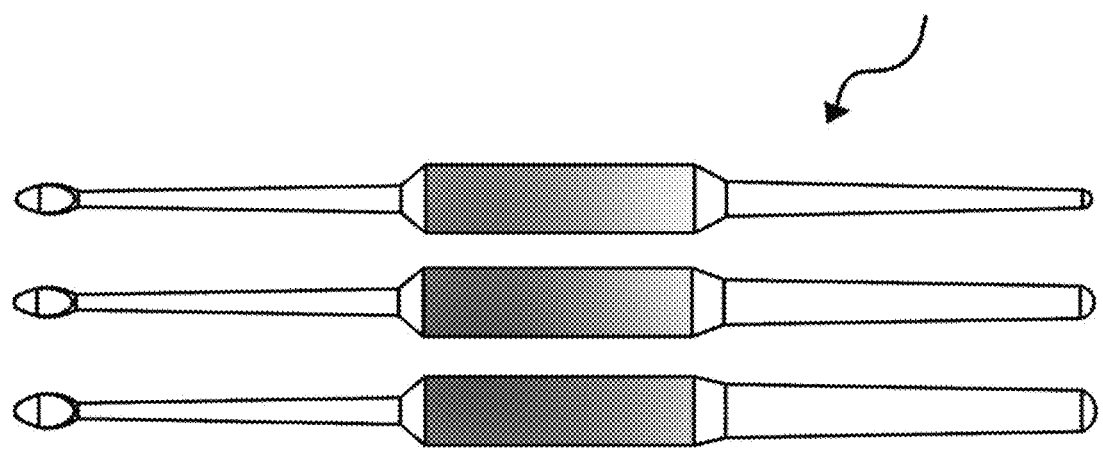
FIG. 26 illustrates an orthogonal view of additional embodiments of dilators.

Referring now to FIG. 9, FIG. 9 illustrates an orthogonal view of the dilators 80 used in conjunction with an embodiment. The dilators 80 used in the system are a set of standard dilators of different sizes used in common surgical procedures related to endoscopic (or arthroscopic) devices. The main purpose of the dilators 80 is to create a pathway for the guiding system 10 to be inserted inside the body without any resistance (or with relatively little resistance), after a small incision is made. There is a space between the superficial sensory nerves and the fascia up above and another space between the fascia and the more superficial tissues. The dilator is inserted in between those two spaces in order to create a tunnel for guiding system 10 and breaks up some of small fibers that might prevent the insertion of the guiding system 10. The dilator lifts up the superficial sensory nerves and therefore potentially reduces chances of iatrogenic injury to those nerves. Dilators of various sizes are provided for opening the incision prior to inserting the guiding system 10 through small incision. FIG. 26 illustrates an orthogonal view of a set of similar dilators 1880.

Figure 10:
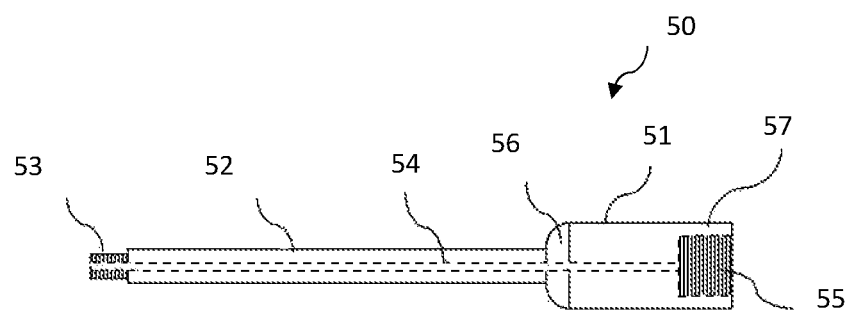
FIG. 10a illustrates an orthogonal side view of a cannula to be used with an endoscope in accordance with one embodiment.
FIG. 10b illustrates a perspective view of the cannula of FIG. 10a in accordance with one embodiment.
Figure 10B:
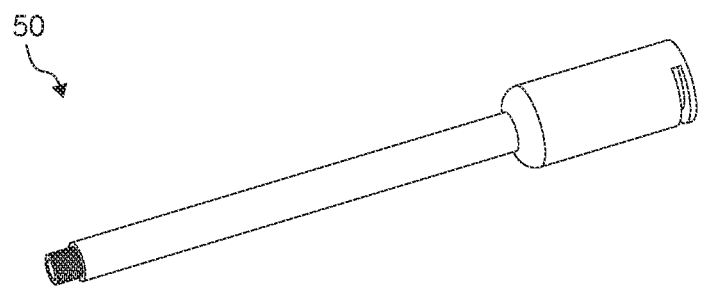

FIGS. 10a and 10b illustrate an orthogonal side view and perspective view respectively of the cannula 50 to be used with the endoscope 60 in accordance with one embodiment. The cannula 50 comprises a first cylindrical sheath 51 having a lower end 57 and an upper end 56. The cannula 50 preferably comprises stainless steel but can comprise any surgically suitable material. The lower end 57 of the first cylindrical sheath 51 is provided with a fastening means (e.g., thread and/or the like) to attach to the proximal end 61 of the endoscope 60. In an example embodiment, a thread portion 55 is provided on the inner diameter of the first cylindrical sheath 51 such that it is sufficient to be fixed to the proximal end 61 of the endoscope 60. The external diameter of the second cylindrical sheath 52 which is attached to the upper end 56 of the first cylindrical sheath 51 is approximately equal to the external diameter of the knife unit 30 so as to avoid any obstruction or resistance while inserting the cannula knife assembly, inside the incision. The front end 53 of the cannula 50 is also provided with a means for fastening the cannula 50 to the extreme end 40 of the tubular sheath 36 of the knife unit 30. In present embodiment, an external thread portion 53 of a diameter approximately equal to the internal diameter of the thread portion at the extreme end 40 of the tubular sheath 36 of the knife unit 30 is illustrated. The cannula 50 has a narrow cylindrical passage 54 extending longitudinally through its length. The diameter of the passage 54 is configured to facilitate the insertion tube 62 of the endoscope 60 pass through it.

Figure 11C:
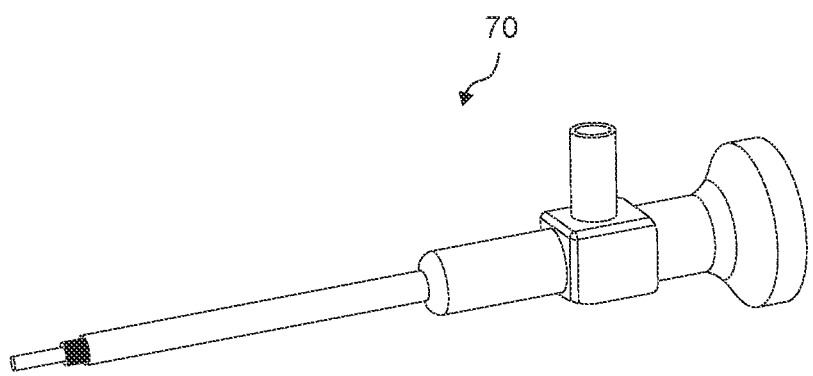

FIG. 11a illustrates an orthogonal side exploded view of the cannula endoscope assembly in accordance with one embodiment. FIG. 11b illustrates an assembled side view thereof. FIG. 11c illustrates an assembled perspective view thereof. The cannula 50 is attached to the proximal end 61 of the endoscope 60 via fastening means as discussed above (e.g., threads). After attaching, the probe head 63 of the endoscope 60 comes out from the front end 53 of the cannula 50 while passing through the second cylindrical sheath 52. The probe head 63 of the endoscope 60 is visible from the front end 53 after being attached to the cannula 50.

Figure 12:
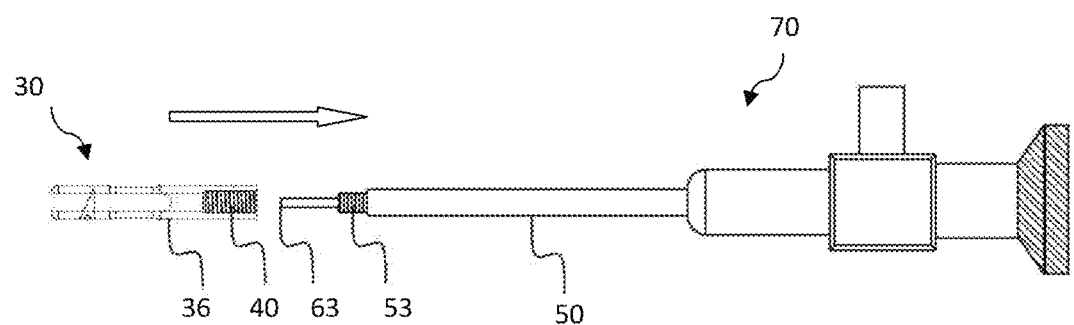
FIG. 12 illustrates an orthogonal side view of a knife unit being attached to the cannula endoscope assembly of FIGS. 11A-11C in accordance with one embodiment.
Figure 13:
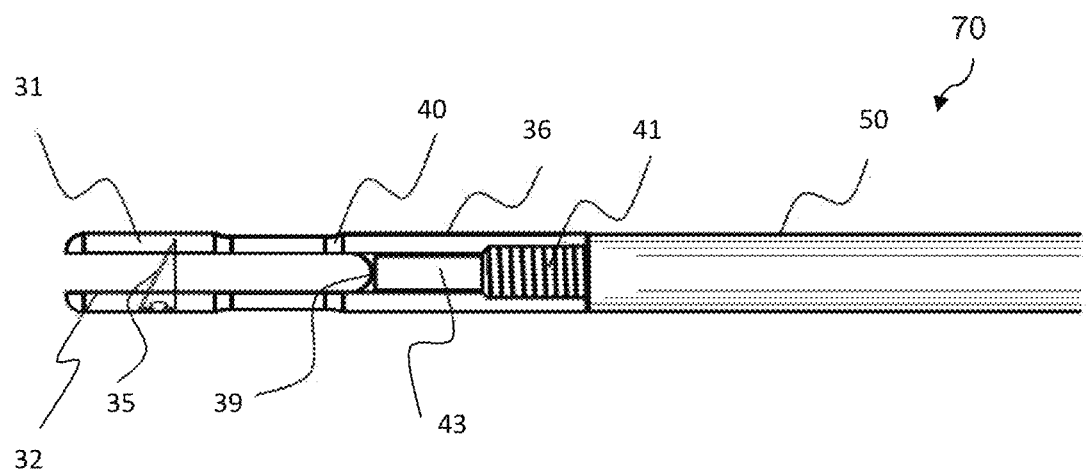
FIG. 13 illustrates another orthogonal side view of the knife unit being attached to the cannula endoscope assembly of FIGS. 11A-11C in accordance with one embodiment.
Figure 27:
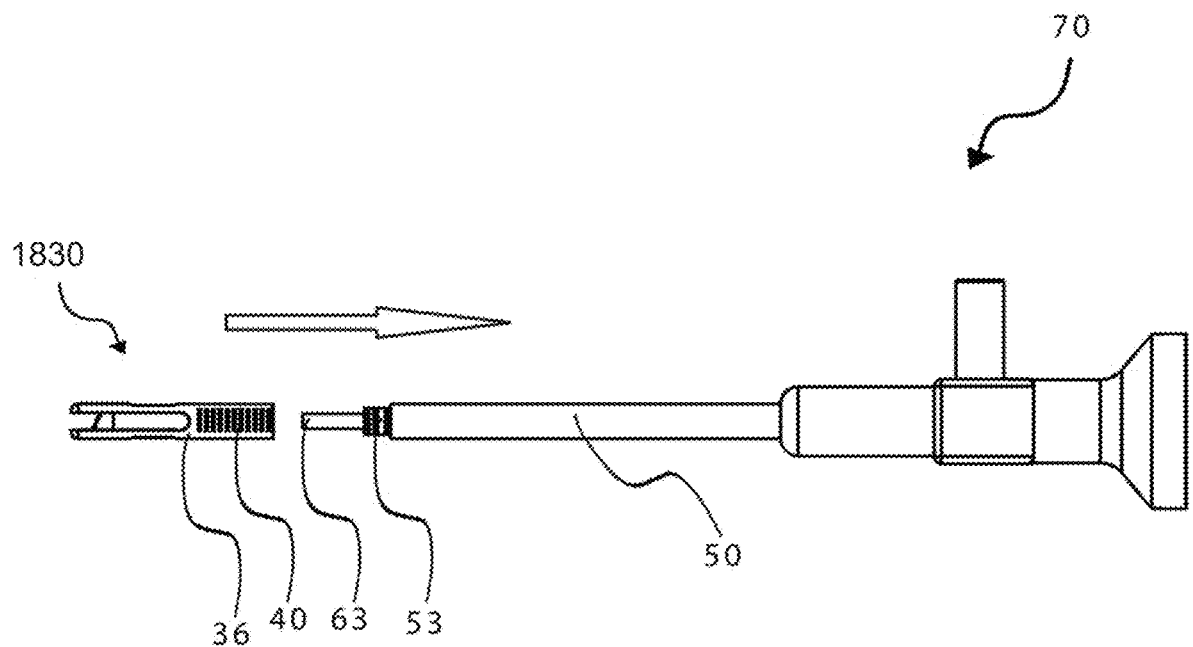
FIG. 27 illustrates an orthogonal side view of the knife unit of FIG. 19 being attached to the cannula endoscope assembly of FIGS. 11A-11C in accordance with one embodiment.
Figure 28:
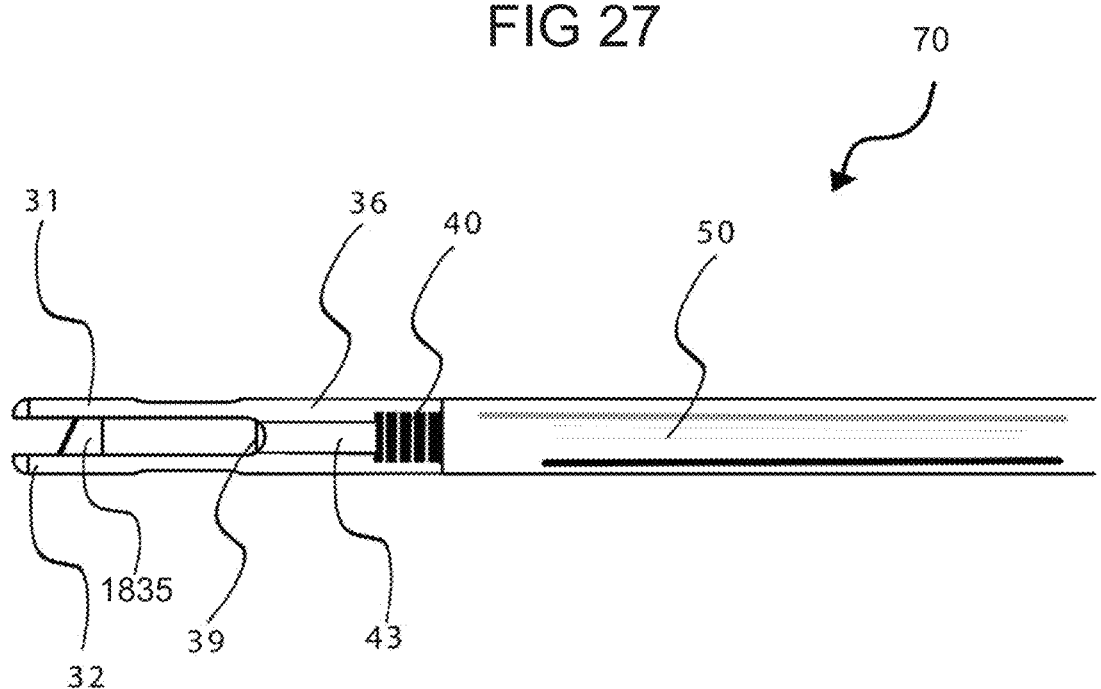
FIG. 28 illustrates another orthogonal side view of the knife unit of FIG. 19 being attached to the cannula endoscope assembly of FIGS. 11A-11C in accordance with one embodiment.

FIG. 12 illustrates an exploded orthogonal side view of the knife unit 30 being attached to the cannula endoscope assembly 70 in accordance with one embodiment. FIG. 13 illustrates a closer view of the knife unit 30 attached to a distal end of the cannula endoscope assembly 70. In further embodiment, the extreme end 40 of the knife unit 30 is further attached to the cannula endoscope assembly 70 through a fastening means. In an example embodiment, threads are provided on the front end 53 of the cannula 50 externally which are introduced into the thread portion 41 of the tubular sheath 36. Any other fastening means can be used for that purpose. The knife unit 30 is attached to the cannula 50 by attaching the extreme end 40 of the knife unit 30 with the front end 53 of the cannula 50. The tubular sheath 36 of the knife unit 30 has an inner diameter sufficient to permit the front end 53 of the cannula 70 assemble into the tubular sheath 36 by fastening means such as thread mechanism and the like. After complete assembling of the knife unit 30 with the cannula 50, the probe head 63 of the endoscope 60 fits inside the aperture 39 of the knife unit 30. The knife unit 30 can be disassembled from the endoscope 60 by unfastening and withdrawing the knife unit 30 from the endoscope 60. In this manner, a blunt or worn out cutting blade 35 may be replaced during a surgical procedure, e.g. for a cutting blade 35 of different configuration. The figure shows the knife unit 30 being attached to the endoscope 60. FIGS. 27 and 28 illustrate similar views to FIGS. 12 and 13, except using the knife unit 1830 of FIG. 19 instead of knife unit 30 of FIG. 2.

Figure 14:
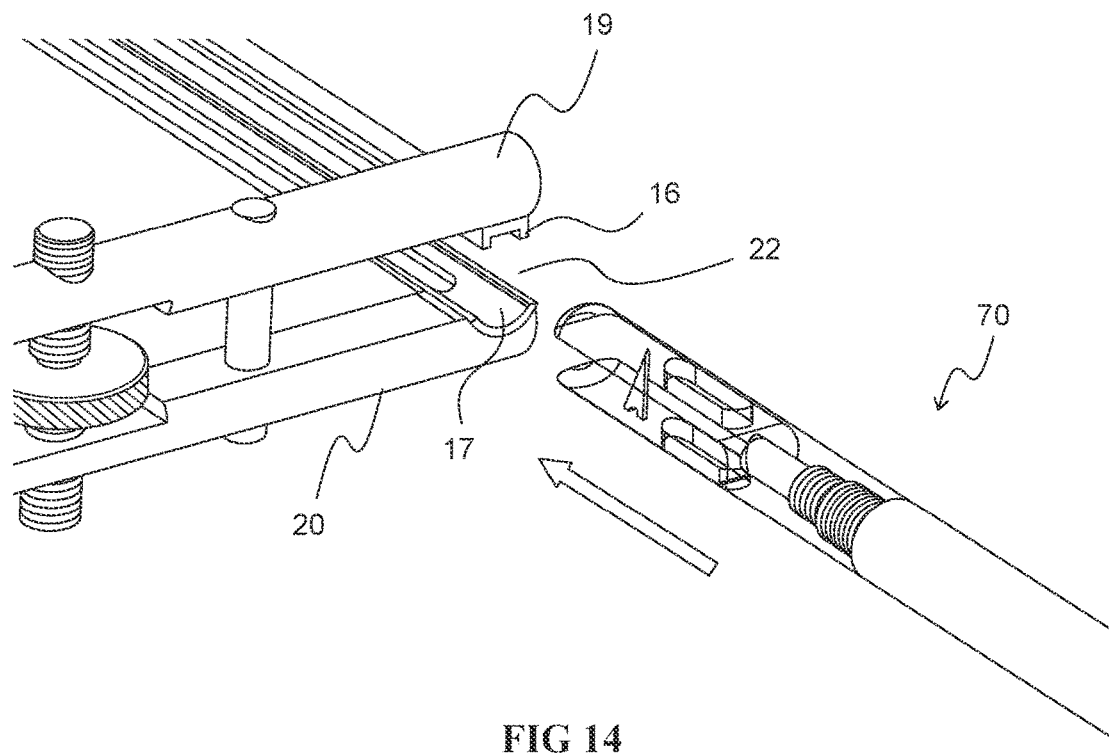
FIG. 14 illustrates a perspective view of the endoscopic knife unit of FIG. 13 while being inserted inside the parallel guides of a guiding system in accordance with one embodiment.
Figure 15:
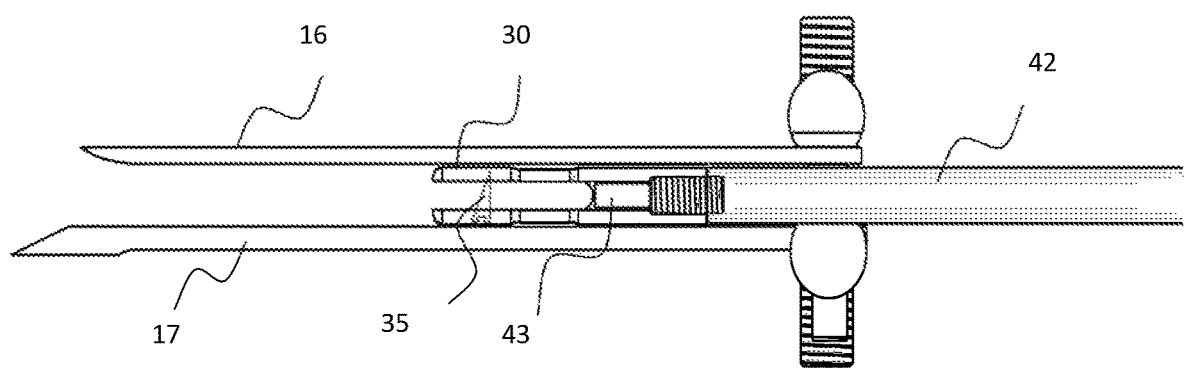
FIG. 15 illustrates a side elevation view of the endoscopic knife unit while being inserted inside the parallel guides of the guiding system of FIG. 14 in accordance with one embodiment.
Figure 29:
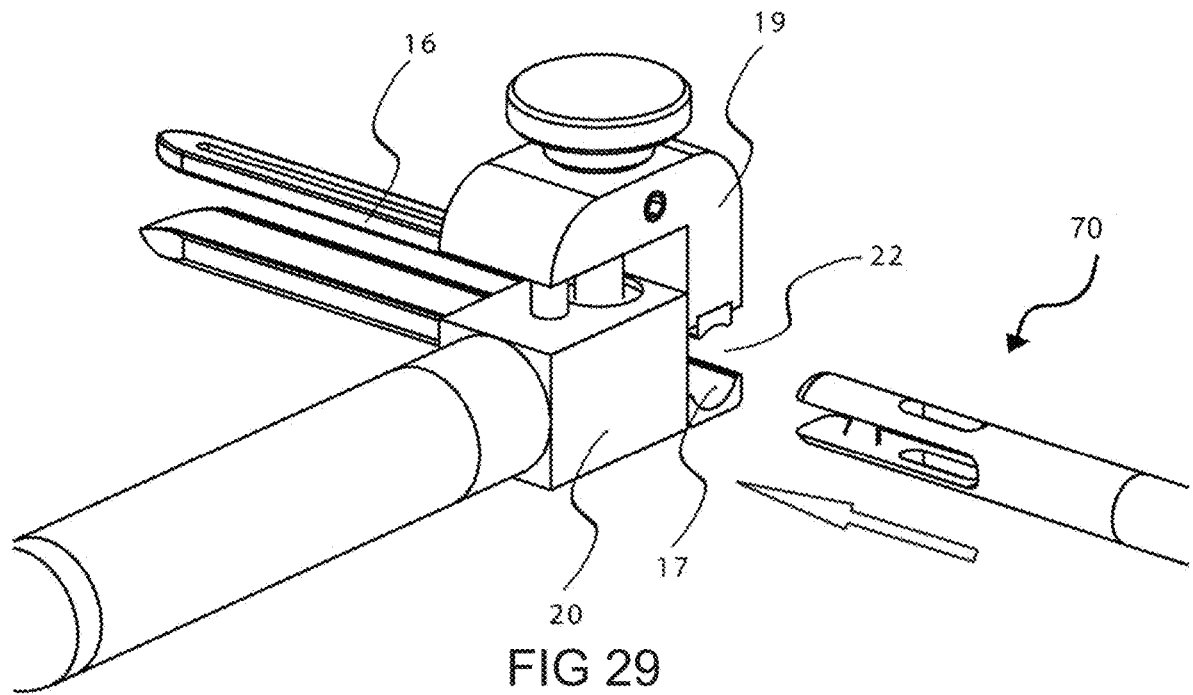
FIG. 29 illustrates a perspective view of the endoscopic knife unit of FIG. 28 while being inserted inside the parallel guides of a guiding system in accordance with one embodiment.
Figure 30:
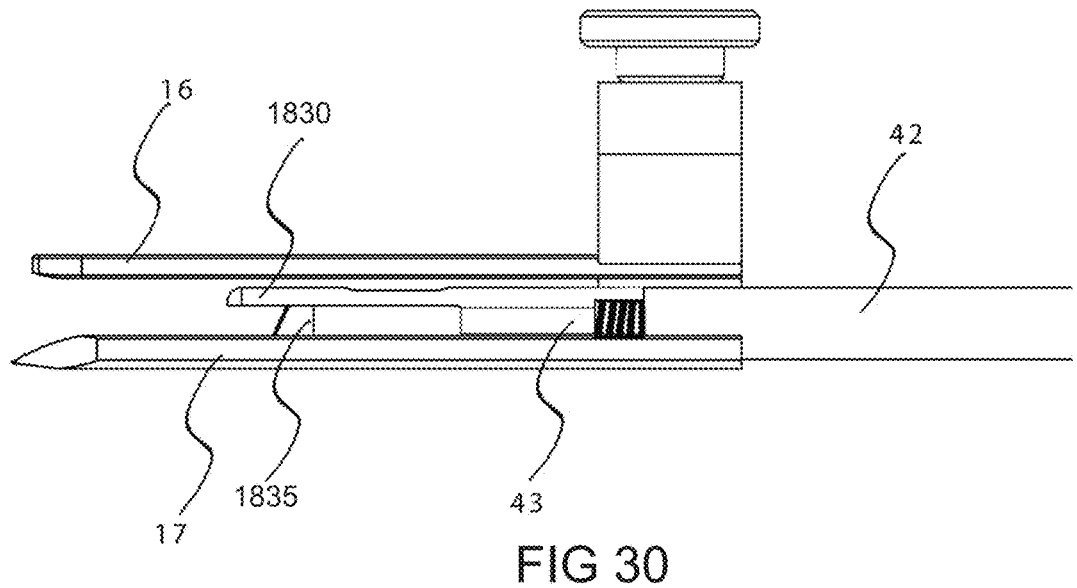
FIG. 30 illustrates a side elevation view of the endoscopic knife unit of FIG. 28 while being inserted inside the parallel guides of the guiding system of FIG. 29 in accordance with one embodiment.

FIG. 14 and FIG. 15 illustrate perspective and side elevation views, respectively, of the endoscopic knife unit 30 while being inserted inside the parallel guides 16, 17 of the guiding system 10 in accordance with one embodiment. After an incision is made through the flesh of a living body, the front portion of parallel guides 16,17 is inserted in closed position through the incision and advanced slowly deep inside the incision. The parallel guides 16, 17 are drifted apart slowly by rotating the adjusting wheel 14. According to an embodiment, after assembling the knife unit 30, cannula 50 and the endoscope 60, the whole preassembled endoscopic knife unit 70 is introduced to the operating site through the circular opening 22 formed by the parallel guides 16, 17 of the guiding system 10. As the cutting blade 35 proceeds through the parallel guides 16, 17, it cuts the fascia in its path while protecting the adjoining tissue against accidental engagement with the cutting blade 35. The surgeon can view the operating site through the video camera attached to the probe head 63 of the endoscope 60 and can easily adjust and position the endoscopic knife unit 30 as it passes through the fascia. Since the endoscope 60 is positioned in between the two parallel guides 16, 17 of the guiding system 10, the knife unit 30 does not move as the endoscope 60 advances towards the operating site. Hence, the undesired movement of the cutting blade 35, and thus the potential danger of accidental cutting of tissue other than at the desired location are avoided. The parallel guides 16, 17 of the guiding system 10 further serve as cannula that remains at a fixed position through the tissue. When required, the surgeon can quickly remove the worn out knife unit 30 attached with the endoscope 60 and can reintroduce a new knife unit 30 without damaging the surrounding tissue. The entire surgical process can take only a few minutes and reduces or completely diminishes the trauma and pain associated with commonly available method wherein cannulas of varied sizes have to be inserted and later replaced with the one of the larger diameter when needed. Moreover, generally available surgical blades do not provide complete protection against accidental damage due to undesirable movement. FIGS. 29 and 30 illustrate perspective and side elevation views, respectively, of the endoscopic knife unit 1830 while being inserted inside the parallel guides 16, 17 of the guiding system 1810 in accordance with one embodiment. The knife unit 1830 and guiding system 1810 operate similarly during surgery to the knife unit 30 and guiding system 10, as described above.

Figure 16:
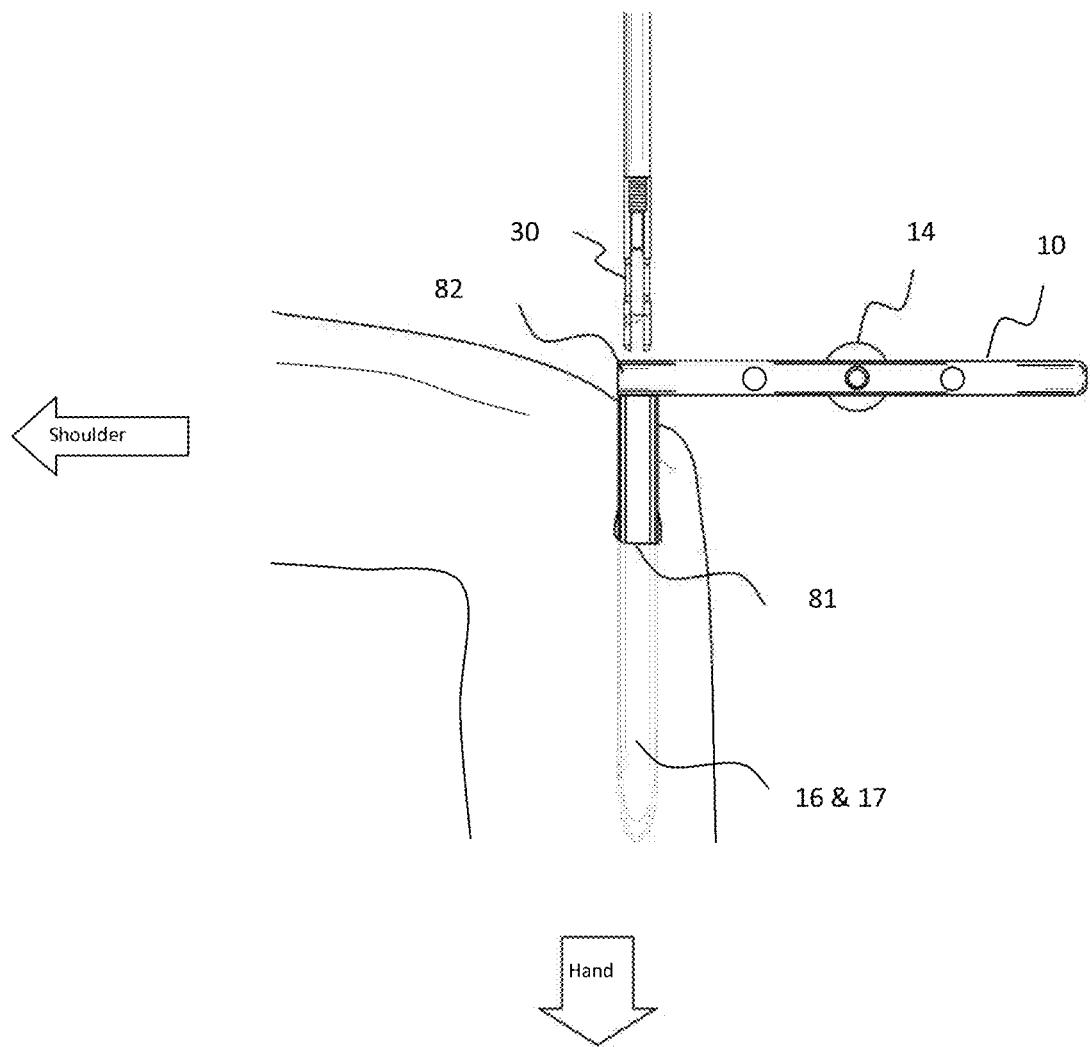
FIG. 16 illustrates an embodiment of a method for performing nerve release surgery.
Figure 31:
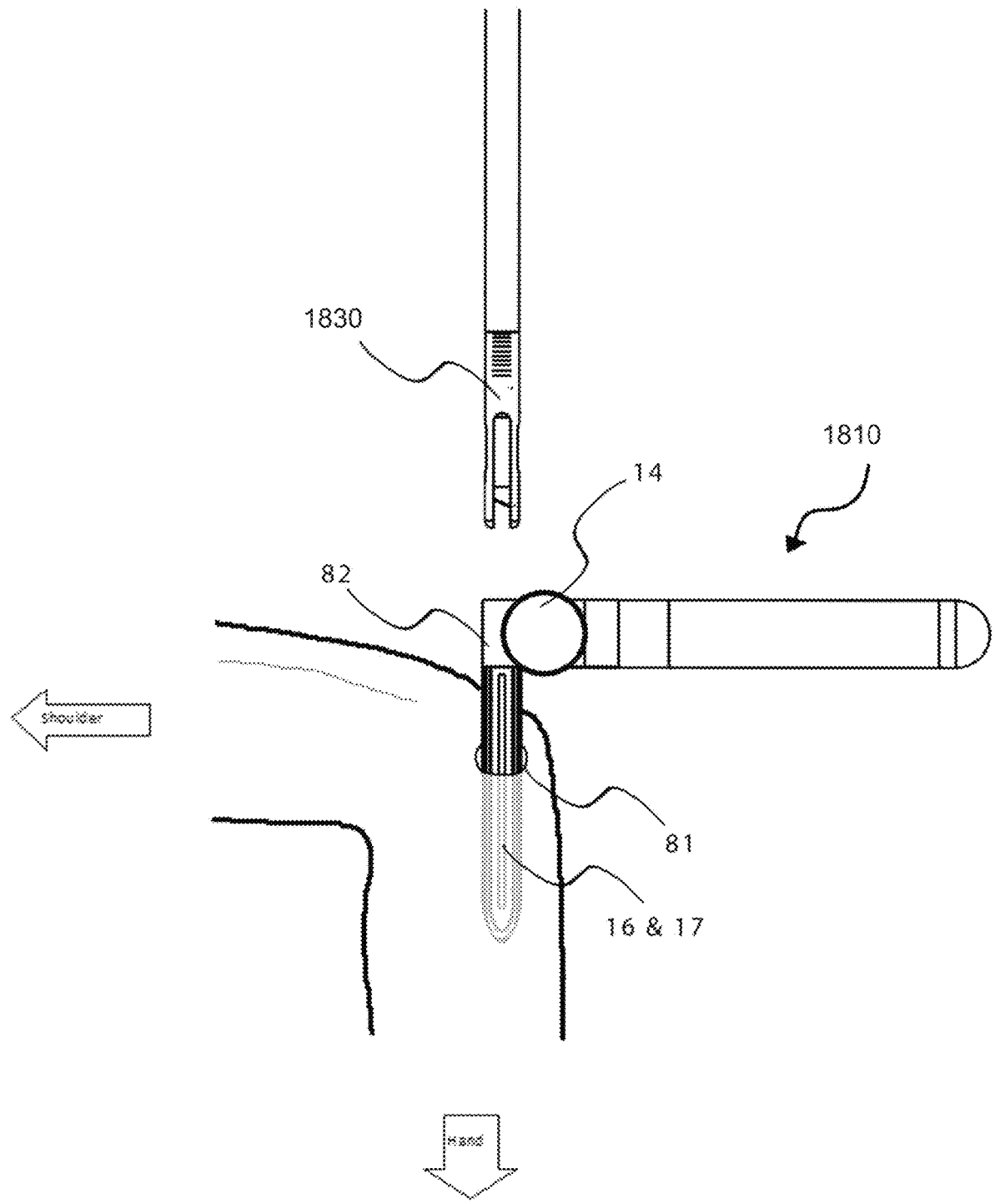
FIG. 31 illustrates another embodiment of a method for performing nerve release surgery.

FIG. 16 illustrates a method for performing nerve release surgery using the system illustrated in FIG. 1. FIG. 31 illustrates a similar method, but using the system illustrated in FIG. 18. The principles described herein can be applied to various nerve decompression surgeries. For the purpose of illustration, the Cubital tunnel release surgery is described herein. The operation is carried out under regional or general anesthesia. The arm is positioned in 90 degree abduction on a standard hand table and the surgeon flexes and supinates the arm to face the cubital tunnel area. The method of the present embodiment for nerve decompression is initiated by palpitation of the ulnar nerve followed by transversely making an incision 81 of approximately 15 mm to 20 mm over the retrocondylar groove. The ulnar nerve is identified which is clearly recognizable by the vasa nervorum. There is a space between the ulnar nerve and the forearm fascia up above and another space between the fascia and the more superficial subcutaneous tissues. A dilator of suitable size is introduced distally about 10 to 12 cm and proximally about 8 to 10 cm into the fascia in those two spaces in order to create a space and to break up some of these small fibers that would prevent the insertion of the parallel guides 16, 17 of the guiding system 10 or 1810. The tunneling is desirably done delicately to protect the antebrachial cutaneous nerve and its branches. The dilator creates a space sufficient for the entry of parallel guides 16, 17 of guiding system 10 or 1810 inside the incision without any resistance and lifts up the superficial sensory nerves while reducing the risk of iatrogenic injury to the proximate nerves. After the space is created, the dilator is removed and front portion of the parallel guides 16, 17 is inserted through the incision 81. Before inserting, the parallel guides 16, 17 are brought closer by rotating the adjusting wheel 14 of the guiding system 10 or 1810. After insertion, the parallel guides 16, 17 are drifted apart slowly by rotating the adjusting wheel 14. At this point, the preassembled endoscopic knife unit 30 or 1830 and the endoscope 42 are introduced to the operating site through the opening formed by the parallel guides 16, 17 of the guiding system 10 or 1810. The surgeon can view the operating site through the video camera 43 attached to the probe head 63 of the endoscope 60 and can easily adjust and position the knife unit 30 or 1830 as it passes through the fascia. The knife unit 30 or 1830 cuts and separates the fascia it passes through. The upper limb 31 and the lower limb 32 disposed on both the sides of the cutting blade 35 or 1835 protect the tissue against accidental cutting engagement with the blade. The parallel guides 16, 17 of the guiding system 10 or 1810 further serve as cannula that remains at a fixed position through the flesh. When required, the surgeon can quickly remove the knife unit 30 or 1830 attached to the endoscope 60 and reintroduce a new knife unit without damaging the surrounding tissue. The entire surgical process can take only a few minutes and reduces or completely diminishes the trauma and pain associated with commonly available methods and apparatuses wherein cannulas of varied sizes have to be inserted and later replaced with one of a larger diameter when needed. After the pressure has been released completely from the operating site, the guiding system is removed and incision is stitched.

FIG. 17 illustrates a screenshot of the operating site as displayed on the display device of the endoscope during the nerve release surgery. When the endoscope 60 is inserted inside the operating site, it starts live streaming of the captured images from the video camera to the display device attached to the probe head 63 of the endoscope 60. The figure shows the upper limb 31 and the lower limb 32 of the knife unit 30 as captured by the probe head 63 of the endoscope 60. The region 71 is the fascia which is being cut and drifted apart by the cutting blade 35 while passing through it. The region 72 is the surrounding tissue as visible through the open slots 33 and 34 on the upper limb 31 and lower limb 32 of the knife unit 30.

The entire process can take only a few minutes and reduces or completely diminishes the trauma and pain associated with commonly available methods and apparatuses for nerve decompression. The system and method described in the present disclosure give excellent results in terms of recovery and postoperative complications.

Various other embodiments are possible within the spirit of the present disclosure and the aforementioned examples and embodiments are just meant to be for explanatory purposes, and in no way intend to limit the scope of the disclosure in any manner. The arm support assembly of the present disclosure can be made from various kinds of materials available in the field and known to a person skilled in the art. Preferably the arm support assembly is made of material that can withstand the temperature and pressure conditions for autoclaving. The disclosure further intends to cover all the equivalent embodiments.

While there is shown and described herein certain specific structure embodying various embodiments, it will be manifest to those skilled in the art that various modifications and rearrangements of the parts may be made without departing from the spirit and scope of the underlying inventive concepts and that the same is not limited to the particular forms herein shown and described.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. Additionally, it is contemplated that various aspects and features of the inventions described can be practiced separately, combined together, or substituted for one another, and that a variety of combination and sub-combinations of the features and aspects can be made and still fall within the scope of the inventions. Thus, it is intended that the scope of the present inventions herein disclosed should not be limited by the particular disclosed embodiments described above, but should be determined only by a fair reading of the claims. Any ranges disclosed herein also encompass any and all overlap, sub-ranges, and combinations thereof. Language such as "up to," "at least," "greater than," "more than," "less than," "between," and the like includes the number recited. Numbers preceded by a term such as "approximately", "about", and "substantially" as used herein include the recited numbers (e.g., about 10%~10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A knife unit for use in endoscopic surgery, the knife unit comprising:
   a tubular sheath extending from a proximal end to a distal end and defining a longitudinal axis, the tubular sheath comprising an aperture extending longitudinally therethrough for receiving a probe head of a medical instrument;
   an upper limb extending distally from the distal end of the tubular sheath;
   a lower limb extending distally from the distal end of the tubular sheath,
   wherein the upper limb and the lower limb are laterally spaced apart from one another; and
   a blade disposed between the upper limb and the lower limb, the blade comprising an upper portion connected to the upper limb and a lower portion connected to the lower limb, the blade further comprising a distal facing cutting edge extending from the upper portion of the blade to the lower portion of the blade,
   wherein the upper limb and the lower limb each comprise a distal end that is positioned distally beyond the cutting edge of the blade,
   wherein the blade further comprises a proximal edge that is positioned distally beyond the distal end of the tubular sheath; and
   wherein the knife unit is configured such that, in a view normal to a plane that includes the longitudinal axis and that is parallel to a side of the blade that extends from the upper limb to the lower limb, an opening extends through the knife unit, the opening defined at least partially by the proximal edge of the blade, an inner edge of the upper limb, and an inner edge of the lower limb.

2. The knife unit of claim 1, wherein the cutting edge of the blade is inclined relative to the longitudinal axis of the tubular sheath.

3. The knife unit of claim 1, wherein the blade is positioned such that, in a view perpendicular to the longitudinal axis of the tubular sheath, the blade passes through the longitudinal axis of the tubular sheath.

4. The knife unit of claim 1, wherein the blade comprises a trapezoidal shape.

5. The knife unit of claim 1, wherein the blade comprises a triangular shape.

6. The knife unit of claim 1, wherein opposing inner surfaces of the upper limb and the lower limb are parallel to one another, with the cutting edge of the blade extending between the opposing inner surfaces of the upper limb and the lower limb.

7. The knife unit of claim 6, wherein the opposing inner surfaces of the upper limb and the lower limb are further parallel to the longitudinal axis of the tubular sheath.

8. The knife unit of claim 1, wherein each of the upper limb and the lower limb comprise an inner surface that extends in a direction parallel to the longitudinal axis of the tubular sheath.

9. The knife unit of claim 1, wherein the upper portion of the blade is secured to the upper limb within a groove of the upper limb, and the lower portion of the blade is secured to the lower limb within a groove of the lower limb.

10. The knife unit of claim 1, wherein the tubular sheath comprises plastic.

11. The knife unit of claim 1, wherein the tubular sheath comprises stainless steel.

12. The knife unit of claim 1, wherein the knife unit is a single use item.

13. A system for performing endoscopic surgery, comprising:
    the knife unit of claim 1; and
    the medical instrument, wherein the medical instrument comprises a shaft, the probe head being positioned at a distal end of the shaft,
    wherein the shaft is sized to be inserted into the aperture of the tubular sheath of the knife unit.

14. The system of claim 13, wherein the knife unit is a single use item.

15. A knife assembly for use in endoscopic surgery, the knife assembly comprising:
    a tubular member having a proximal end and a distal end, the tubular member comprising a lumen extending longitudinally therethrough and defining a longitudinal axis;
    an upper limb extending distally from the distal end of the tubular member;
    a lower limb extending distally from the distal end of the tubular member; and
    a blade disposed between the upper limb and the lower limb, the blade comprising an upper portion that is in a fixed position with respect to the upper limb and a lower portion that is in a fixed position with respect to the lower limb,
    wherein the blade further comprises a distal facing cutting edge and a proximal edge, the proximal edge being positioned distally beyond the distal end of the tubular member, and the cutting edge extending from the upper portion of the blade to the lower portion of the blade, and
    wherein the knife assembly is configured such that, in a view normal to a plane that includes the longitudinal axis and that is parallel to a side of the blade that extends from the upper limb to the lower limb, an opening extends through the knife assembly, the opening defined at least partially by the proximal edge of the blade, an inner edge of the upper limb, and an inner edge of the lower limb.

16. The knife assembly of claim 15, wherein the upper limb and the lower limb each comprise a distal end that is positioned distally beyond the cutting edge of the blade.

17. The knife assembly of claim 15, wherein the blade comprises a trapezoidal shape.

* * * * *